US006392119B1

(12) United States Patent
Gutterson et al.

(10) Patent No.: US 6,392,119 B1
(45) Date of Patent: May 21, 2002

(54) TWO COMPONENT PLANT CELL LETHALITY METHODS AND COMPOSITIONS

(75) Inventors: Neal Gutterson, Oakland; Ed Ralston, Pleasant Hill, both of CA (US)

(73) Assignee: DNA Plant Technology Corporation, Oakland, CA (US)

( * ) Notice: Subject to any disclaimer, the term of this patent is extended or adjusted under 35 U.S.C. 154(b) by 0 days.

(21) Appl. No.: 09/012,895

(22) Filed: Jan. 23, 1998

Related U.S. Application Data

(60) Provisional application No. 60/036,483, filed on Jan. 24, 1997.

(51) Int. Cl.$^7$ .......................... C12N 15/82; C12N 5/04; C12N 15/29; A01H 5/00; A01H 5/10
(52) U.S. Cl. .................... 800/278; 800/288; 800/290; 800/295; 800/298; 800/300; 800/303; 435/69.1; 435/440; 435/468; 435/469; 435/410; 435/418; 435/419
(58) Field of Search .......................... 800/278, 303, 800/260, 288, 290, 295, 298, 300; 435/69.1, 440, 468, 469, 410, 418, 419

(56) References Cited

FOREIGN PATENT DOCUMENTS

| WO | WO 91/15585 | 10/1991 | ........... C12N/15/31 |
|---|---|---|---|
| WO | WO 92/21757 | 12/1992 | |
| WO | WO 93/10251 | 5/1993 | |
| WO | WO 93/18170 | 9/1993 | |
| WO | WO 93/25695 | * 12/1993 | ........... C12N/15/82 |
| WO | WO 94/03619 | 2/1994 | ........... C12N/15/82 |
| WO | WO 94/10320 | 5/1994 | |
| WO | WO 94/17194 | 8/1994 | |
| WO | WO 96/26283 | 8/1996 | |
| WO | WO 98/37211 | 8/1998 | ........... C12N/15/82 |

OTHER PUBLICATIONS

Gossen et al. Proc. Natl. Acad. Sci. 1992. vol. 89:5547–5551, 1992.*
Odell et al. Plant Physiol. 1994. vol. 106: 447–458.*
Dekeyser et al. The Plant Cell. 1990. vol. 2: 591–602.*
Carvalho et al. The EMBO J. 1992. vol. 11: 2595–2602.*
National Science Foundation SBIR grant application "Genetic Engineering of Regulated Seedlessness in Seed Propagated Crops", effective Award Date Feb. 1, 1996, Principal Investigator Neal Gutterson, Co–Principal Investigator Alison Morgan.
Odell et al., "Seed–Specific Gene Activation Mediated by the Cre/lox Site–Specific Recombination System", *Plant Physiol* 106:447–458 (1994).
Strittmatter, Günter, et al. (1995) "Inhibition of Fungal Disease Development in Plants by Engineering Controlled Cell Death", *Biotechnology* 13:1085–1089.

Herrera, Pedro–Luis, et al. (1994) "Ablation of islet endocrine cells by targeted expression of hormone–promoter–driven toxigenes", *Proc. Natl. Acad. Sci. USA*, 91:12999–13003.
Brady, Hugh J., et al. (1994) "Specific ablation of human immunodeficiency virus Tat–expressing cells by conditionally toxic retroviruses", *Proc. Natl. Acad. Sci. USA*, 91:365–369.
Panchal, Rekha G., et al. (1996) "Tumor protease–activated, pore–forming toxins from a combinatorial library", *Nature Biotechnology*, 14:852–856.
Weinmann, Pamela, et al. (1994) "A chimeric transactivator allows tetracycline–responsive gene expression in whole plants", *The Plant Journal*, 5(4):559–569.
Bayley, Christopher, C., et al. (1992) "Exchange of gene activity in transgenic plants catalyzed by the Cre–lox site–specific recombination system", *Plant Molecular Biology*, 18:353–361.
Carroll, Bernard J., et al. (1995) "Germinal Transpositions of the Maize Element Dissociation From T–DNA Loci in Tomato", *Genetics*, 139:407–429.
Mariani, Celestina, et al. (1990) "Induction of male sterility in plants by a chimaeric ribonuclease gene", *Nature*, 347:737–741.
Mauguen, Y., et al. (1982) "Molecular structure of a new family of ribonucleases", *Nature*, 297:162–164.
Fujii, Tsutomu, et al. (1995) "Cloning and Nucleotide Sequence of the Ribonuclease $T_1$ Gene (rntA) from *Aspergillus oryzae* and Its Expression in *Saccharomyces cerevisiae* and *Asperigillus oryzae*", *Biosci. Biotech. Biochem.*, 59:1869–1874.
Sancho, Javier, et al. (1992) "Dissection of an Enzyme by Protein Engineering—The N and C–Terminal Fragments of Barnase Form A Native–like Complex with Restored Enzymic Activity", *J. Mol. Biol.*, 224:741–747.
Serrano, Luis, et al. (1993) "Step–wise Mutation of Barnase to Binase—A Procedure for Engineering Increased Stability of Proteins and an Experimental Analysis of the Evolution of Protein Stability", *J. Mol. Biol.*, 233:305–312.
Hammond–Kosack, Kim E., et al. (1994) "Developmentally regulated cell death on expression of the fungal avirulence gene Avr9 in tomato seedlings carrying the disease–resistance gene Cf–9", *Proc. Natl. Acad. Sci. USA*, 91:10445–10449.
Hartley, Robert W. (1988) "Barnase and Barstar—Expression of Its Cloned Inhibitor Permits Expression of a Cloned Ribonuclease", *J. Mol. Biol.*, 202:913–915.

* cited by examiner

Primary Examiner—Amy J. Nelson
Assistant Examiner—Ousama M. F. Zaghmout
(74) *Attorney, Agent, or Firm*—Townsend and Townsend and Crew LLP

(57) ABSTRACT

The present invention is directed to methods for inhibiting the growth or killing cell in an organism, particularly plants. Genetically engineered cells and which allow for killing or provision of a beneficial effect to specified cells are also provided.

25 Claims, 1 Drawing Sheet

TWO COMPONENT PLANT CELL LETHALITY METHODS AND COMPOSITIONS

CROSS REFERENCE TO RELATED APPLICATIONS

This application claims the benefit of U.S. application Ser. No. 60/036,483, filed Jan. 24, 1997.

FEDERALLY SPONSORED RESEARCH OR DEVELOPMENT

Not applicable.

FIELD OF THE INVENTION

The present invention relates generally to methods for preventing the growth of specific cells in a multi-cellular eukaryote, particularly plant cells. Recombinantly modified plant cells for expression of cytotoxic genes are also provided.

BACKGROUND OF THE INVENTION

One key objective of plant genetic engineering is to create novel traits either through expression of an introduced gene or by silencing of an endogenous gene. One use of targeted gene expression is the elimination of specific plant cells through the production of an enzyme that is lethal to the cell. In order to eliminate only a specific set of cells, it is necessary that expression of a potentially lethal function be controlled precisely such that the cell-lethal function is expressed only in the cells targeted for elimination and in no others.

Several different approaches have now been attempted to create novel plant traits using a single component cell lethality system. In one-component cell lethality systems, specific cell types are targeted for elimination using a single promoter driving expression of a cytotoxic gene product. These approaches are initiated by the characterization of promoters that are active in specific tissues or under specific conditions. For example, male sterility has been demonstrated using promoters active in tapetal tissue. A number of different promoters have been identified that are expressed in tapetal tissue and other tissue. A further example is the use of cell lethality to create disease resistance via a hypersensitive response. A number of promoters have been characterized by different workers that are induced upon pathogen infection. A further example is the attempt to create nematode resistance by killing giant cells, the specific root cells upon which cyst and root knot nematodes feed. A number of promoters have been characterized by different workers that are induced in giant cells, but again sufficient promoter specificity has been difficult to achieve.

In one example (Strittmatter et al., *Bio/Technology* 13:1085–90 (1995)), the workers cite the difficulty of creating transgenic plants using a construct containing a ribonuclease coding sequence (obtained from *Bacillus amyloliquifaciens*, barnase) under the control of a promoter induced upon infection with the fungus *Phytophthora infestans*. Their solution to the difficulty was to express a protective function, barstar, under the control of a constitutive promoter that would hopefully protect non-infected cells, but allow infected cells to be killed. A further example is the attempt to create nematode resistance by killing the specific root cells upon which cyst and root knot nematodes feed, as described in WO 92/21757, WO 93/10251, WO 93/18170, WO 94/10320, and WO 94/17194. A number of promoters have been characterized by different workers that are induced in specialized nematode feeding cells, but again sufficient promoter specificity has been difficult to achieve.

In one case (WO 93/10251), the difficulty of obtaining sufficient promoter specificity is addressed through expression of a protective function in cells other than the target cells. Another example of the protective approach is described in WO 96/26283, which described the production of male sterility using the tapetal specific promoter TA29 from tobacco to program expression of barnase. As in the example above, the protective function for the barnase protein is the barstar protein, whose expression is sought in non-target tissues. Unfortunately, for many potentially useful cell-lethal functions, protective functions are not available. In order to make a protective approach work, it is necessary to identify a second promoter with the requisite "inverse" specificity.

In vertebrates similar cell lethality approaches have been reported to ablate specific cell types or tissue types as an experimental tool, or to kill cells involved in a disease state, such as HIV-infected cells or metastatic cancer cells. The principal cell lethality function chosen for cell ablation is the diphtheria toxin (DT) A chain, which adenoribosylates elongation factor EF-2, thus blocking protein synthesis. Herrera et al., *Proc. Natl. Acad. Sci., USA* 91:12999–13003 (1994). Because of the extreme toxicity of the DT A chain, precise expression is critical. An approach that has been taken in therapeutic situations is the specific introduction and/or expression of a thymidine kinase (tk) gene. The tk gene product is a conditional cell-lethal function, requiring the presence of a nucleoside analog such as ganciclovir for lethality. Brady et al., *Proc. Natl. Acad. Sci., USA* 91:365–69 (1994) describe the use of this approach for specific ablation of human immunodeficiency virus Tat-expressing cells following introduction of a tk gene whose expression is under control of the Tat protein and treatment with ganciclovir.

In developing ways to kill specific subpopulations of cells within an organism, such as metastatic cancer cells in a mammal, the requirement of "twofold specificity", has been recognized. Panchal et al., *Nature Biotechnol.* 14:852–56 (1996). The approach taken by Panchal et al. was to use immunorecognition of the surface of cancer cells as the first level of specificity, and specific protease activities of cancer cells as the second level of specificity.

What is needed in the art are compositions and methods which provide selective elimination or inhibition of growth of a selected cell type in an organism, for example, in a plant. The present invention provides these and other advantages.

SUMMARY OF THE INVENTION

In one aspect, the present invention is directed to a plant cell. The plant cell comprises a first expression cassette comprising a first non-constitutive plant promoter operably linked to a polynucleotide encoding a first polypeptide and a second expression cassette comprising a second non-constitutive plant promoter operably linked to a polynucleotide encoding a second polypeptide. At least the first or the second expression cassette is heterologous to the cell. Further, the first and second promoters have different but overlapping specificities such that the first and second polypeptides are expressed in the same cell.

In some embodiments, the presence of the first and second polypeptides in the same cell impairs cellular function. In some embodiments, the first and second polypeptides each comprise a separate subsequence of a single functional polypeptide. The functional polypeptide can be a ribonuclease such as Barnase, or T1. The functional polypeptide be modified to have enhanced stability. In one embodiment, the enhanced stability barnase is bn3-2 and bn5-2. In additional embodiments of the plant cell, the first polypeptide is an avirulence gene product derived from a plant pathogen and the second polypeptide is a resistance gene product associated with the avirulence gene.

For example, first polypeptide can be avr9 and the second polypeptide Cf9. The functional polypeptide can be a nuclease or colicin. In some plant cell embodiments, the first or the second promoter is a tissue-specific promoter such as when each is functional in seeds or tapetal cells. In some embodiments, the first or second promoter is induced following interaction with a plant pathogen or pest.

In another aspect, the present invention relates to a plant cell comprising a first expression cassette comprising a first plant promoter operably linked to a polynucleotide encoding a first polypeptide and a second expression cassette comprising a second plant promoter operably linked to a polynucleotide encoding a second polypeptide. The first and second polypeptides each comprise a separate subsequence of a single functional polypeptide.

Often, the functional polypeptide impairs cellular function. In some embodiments, the first and second promoters have different but overlapping specificities such that the first and second polypeptides are expressed in the same cell.

In another aspect, the present invention relates to a method for modifying the cellular function of a plant cell. The method comprises the steps of introducing into the cell a first expression cassette comprising a first non-constitutive plant promoter operably linked to a polynucleotide encoding a first polypeptide and a second expression cassette comprising a second non-constitutive plant promoter operably linked to a polynucleotide encoding a second polypeptide, wherein the first and second promoters have different but overlapping specificities such that the first and second polypeptides are expressed in the same cell. The first or the second expression cassettes can be introduced into the plant cell through a sexual cross.

In yet another aspect, the present invention relates to a method of modifying cellular function in a plant cell. The method comprises the steps of introducing into a plant cell a first expression cassette comprising a first plant promoter operably linked to a polynucleotide encoding a first non-functional polypeptide and a second expression cassette comprising a second plant promoter operably linked to a polynucleotide encoding a second non-functional polypeptide, wherein the first and second polypeptides each comprise a separate subsequence of a single functional polypeptide. Often, the first and second promoters have different but overlapping specificities such that the first and second polypeptides are expressed in the same cell.

In a further aspect, the present invention is directed to a method for preventing the growth of a eukaryotic cell. The method comprises the steps of introducing into the cell, a first expression cassette comprising a first tissue-specific plant promoter operably linked to a polynucleotide encoding a first polypeptide and a second expression cassette comprising a second tissue-specific plant promoter operably linked to a polynucleotide encoding a second polypeptide, wherein the first and second promoters are functional in the cell and presence of the first and second polypeptides in a cell impairs cellular function. In some embodiments the cell is a mammalian cell. The mammalian cell can be in a non-human animal. Often, the first and second expression cassettes are introduced into the cell using a retroviral vector.

DETAILED DESCRIPTION OF THE INVENTION

Figure 1:
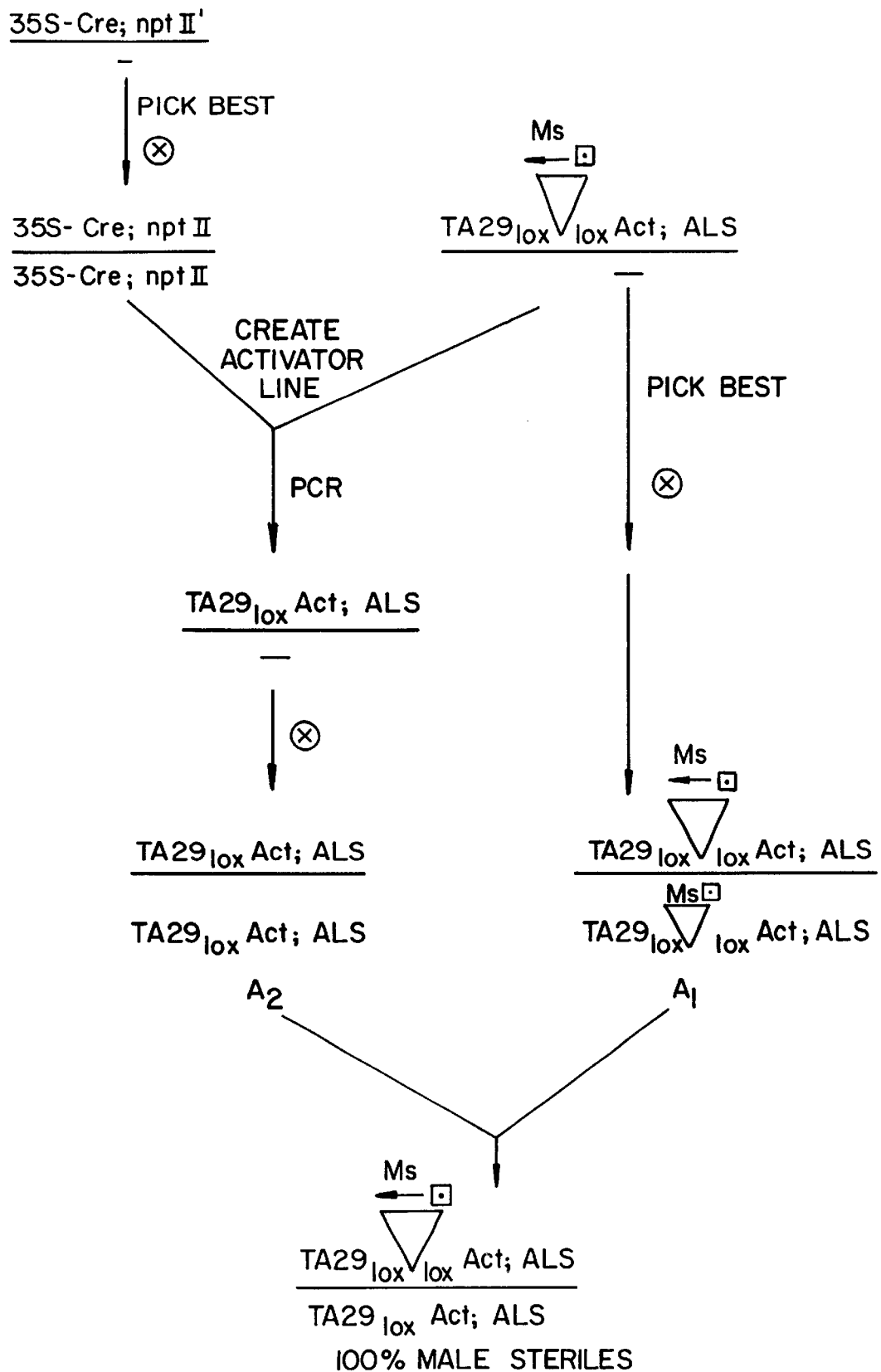
FIG. 1 shows how the allelic variants of p-Mon-Avr9 or TA29-Cf9 containing sublines ($A_1$ and $A_2$) are created using the cre/lox recombinase system and their use in producing male steriles. ALS=acetolactate synthase.

The present invention provides methods for inhibiting the growth or killing of specified eukaryotic cells in multicellular eukaryotic organisms, particularly plants. More specifically, the present invention relates to plant cells comprising at least two expression cassettes operably linked to polynucleotides which when expressed provide a desired effect to specific tissue or cell types. The desired effect can impair cellular function or can be beneficial to the cell (e.g., resistance to plant pathogens or pests). The expression cassettes can occupy the same or different loci of chromosome homologs, or be located on different chromosomes or elsewhere as part of the genome. The present invention provides novel methods for producing plants which can utilize the multi-component system described herein, and embraces the plants so produced and methods of their use.

In contrast to one-component lethality systems in which the use of individual promoters drives expression of a cytotoxic polypeptide, the two or more component lethality/inhibitory methods of the present invention employs two or more promoters having overlapping but distinct tissue-specific expression. This system provides a greater degree of control in targeting a desired function to selected cells than one-component systems. Two or more component systems will typically be optimized by consideration of the following: 1) the desired effect should be cell autonomous; 2) the desired effect should not be dependent upon any other cellular function; 3) the desired effect should be a sensitive function of the level of the associated components.

Methods of the present invention provide means to maintain inbred lines in a hybrid system in which there is no inhibitory or lethality expressed in either inbred line. However, crossing these inbred lines yields a hybrid having the inhibitory or lethal phenotype. The present invention also provides a means to produce a lethal or inhibitory effect in a highly tissue-specific, condition-specific, or developmental stage-specific manner, using two different promoters with overlapping specificity to obtain the necessary specificity. The resulting invention has utility, for example, in creating and maintaining male sterile and female sterile plants.

DEFINITIONS

Units, prefixes, and symbols can be denoted in their SI accepted form. Numeric ranges are inclusive of the numbers defining the range. The headings provided herein are not limitations of the various aspects or embodiments of the invention which can be had by reference to the specification as a whole. Accordingly, the terms defined immediately below are more fully defined by reference to the specification in its entirety.

As used herein, the term "plant" includes reference to whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

As used herein "operably linked" includes reference to a functional linkage between a promoter and a second sequence, wherein the promoter sequence initiates and mediates transcription of the DNA sequence corresponding to the RNA sequence which is typically transcribed into a polypeptide. Generally, operably linked means that the nucleic acid sequences being linked are contiguous and, where necessary to join two protein coding regions, contiguous and in the same reading frame.

As used herein, a "expression cassette" is a nucleic acid construct, generated recombinantly or synthetically, with a series of specified nucleic acid elements which permit transcription of a particular nucleic acid in a target cell. The expression cassette can be incorporated into a plasmid, chromosome, mitochondrial DNA, plastid DNA, virus, or nucleic acid fragment. Typically, the expression cassette portion of the expression vector includes, among other sequences, a nucleic acid to be transcribed, and a promoter.

As used herein, "lethal" or "impairs cellular function" includes reference to polynucleotide(s) or polypeptide(s) that are cytotoxic to an extent that kills cells or inhibits cell division or differentiation. Thus, "lethal" or "impairs cellular function" includes reference either to 1) the disruption of a cell through perturbation of some function of the cell or by degradation of a component of the cell, or 2) to the prevention of continued growth of a cell through perturbation of some function of the cell or degradation of some component of the cell. By way of example, but not limitation, typical cellular functions in the context of the instant invention are protein synthesis, RNA synthesis, maintenance of osmotic competence, lipid synthesis, DNA synthesis. Typical cellular components subject to degradation in the context of the instant invention are proteins, carbohydrates, membranes, deoxyribonucleic acids, ribonucleic acids.

As used herein, "beneficial" includes reference to polynucleotide(s) or polypeptide(s) that impart a protective effect to a cell. In plants, a beneficial effect includes resistance to environmental stresses including, but not limited to, plant pathogens, pests, drought, heavy metals, and salt.

As used herein, "heterologous" is a nucleic acid that originates from a foreign species, or, if from the same species, is substantially modified from its original form. For example, a promoter operably linked to a heterologous structural gene is from a species different from that from which the structural gene was derived, or, if from the same species, one or both are substantially modified from their original form. Thus, a "heterologous expression cassette" is one that comprises at least one element not endogenous to the species or sub-species in which it is introduced.

As used herein, "polynucleotide" and "nucleic acid" includes reference to both double stranded and single stranded DNA or RNA. The terms also refer to synthetically or recombinantly derived sequences essentially free of non-nucleic acid contamination. A polynucleotide can be a gene subsequence or a full length gene (cDNA or genomic). Unless specifically limited, the term encompasses nucleic acids containing known analogues of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

The term "enhanced stability" refers to a polypeptide that has been modified so that one or more of the amino acids has been changed relative to the wild type polypeptide. Such modifications provide enhanced stability to the polypeptide, either alone or in combination with another polypeptide. Enhanced stability includes, e.g., enhanced thermal stability, enhanced activity at lower concentrations, enhanced active site activity, and the like.

As used herein, "functional" includes reference to an activity sufficient to produce a desired effect. Thus, for example, a promoter functional in a specified cell will drive expression to the desired levels. A "functional polypeptide" will have the activity to achieve a desired result, such as cell inhibition or death. Alternatively, a functional polypeptide will provide the cell with a beneficial or therapeutic effect, such as resistance to plant pests or disease. In some embodiments in which a functional polypeptide (e.g., a ribonuclease such as barnase) is produced in cells comprising 2 or more expression cassettes of the invention, an active expression cassette produces a "functional polypeptide" as defined herein. Thus reference to a particular protein or "functional polypeptide" includes the naturally occurring protein or a protein produced in a cell that has the substantially the same activity as the naturally ocurring protein. "Functional polypeptides" of the invention also include modified polypeptides (with amino acid substitutions, both conservative and non-conservative) that have the same activity as a wild-type or unmodified polypeptide.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that initiate transcription only in certain tissues, such as leaves, roots, fruit, seeds, tapetal tissue, anthers, stigmas, or flowers. Such promoters are referred to as "tissue specific". A "cell type" specific promoter is primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, cell type specific, and inducible promoters constitute the class of "non-constitutive" promoters. A "constitutive" promoter is a promoter which is active under most environmental conditions.

Plant Compositions and Methods

The present invention has use over a broad range of types of plants, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum and Datura.

Plant cells of the present invention comprise two or more expression cassettes. When an expression cassette of the present invention is in a cell in which the promoter is functional, the promoter drives expression of the operably linked polynucleotide. Such an expression is a functional expression cassette. When the promoters of both expression cassettes are functional in a cell two "functional transcripts" are made, at least one of which is typically translated to a "functional polypeptide". As a result, for example, cell function is disrupted such that the cell is inhibited or killed. Individually, neither of the expression cassettes is capable of causing the desired result. In some embodiments, the presence in the cell of all functional expression cassettes of the two or more component system yields an inhibitory or cytotoxic effect upon the cell. In some embodiments, the two or more (multi) component system of the invention yields a beneficial effect, e.g., resistance to a plant pathogen or pest.

In some embodiments, one of the expression cassettes is able to express its operably linked polynucleotide in the absence of the other collaborating expression cassette. The collaborating expression cassette requires the presence of the polypeptide expressed by its partner expression cassette to become functional; typically the product of this inducible expression cassette is by itself lethal or inhibitory. For example, the polypeptide may be an activator polypeptide as in the tet repressor/VP16 activator fusion as discussed in Weinmann et al., *The Plant Journal*, 5(4):559–569 (1994).

The expression cassettes of the multi-component cell lethality system of the present invention are DNA or RNA constructs which can be cloned and/or synthesized by any number of standard techniques. An expression cassette will typically comprise transcriptional and translational initiation regulatory sequences which will direct the transcription of the polynucleotide encoding a non-lethal polypeptide in the intended tissues of the transformed plant. Such nucleic acid constructs may be introduced into the genome of the desired plant host by a variety of conventional techniques. Techniques for transforming a wide variety of higher plant species are well known and described in the technical and scientific literature. See, e.g., Weising et al. *Ann. Rev. Genet.* 22:421–477 (1988).

For example, the DNA or RNA nucleic acid construct may be introduced directly into the genomic DNA of the plant cell using techniques such as electroporation and microinjection of plant cell protoplasts, or the nucleic acid constructs can be introduced directly to plant tissue using ballistic methods, such as DNA particle bombardment. Alternatively, the nucleic acid constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch et al. *Science*, 233:496–498 (1984), and Fraley et al. *Proc. Natl. Acad. Sci. USA* 80:4803 (1983).

Microinjection techniques are known in the art and well described in the scientific and patent literature. The introduction of DNA constructs using polyethylene glycol precipitation is described in Paszkowski et al. *EMBO J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

The expression cassettes of the present invention can comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulforon or Basta.

The two or more components of the lethality system of the present invention can be introduced randomly into the plant genome, or as alleles of each other at a single locus of a homologous pair. In some embodiments of the present invention, each of the expression cassettes are located at the same locus on each chromosome of a homologous pair. A particularly preferred means of introducing each expression cassette at the same locus employs the cre/lox recombinase system. Bayley et al., *Plant Molecular Biology* 18:353–361

(1992). The cre/lox system allows the introduction of a precursor expression cassette which can subsequently be manipulated via cre recombinase to remove a subsequence of that precursor cassette. In this way alternate alleles can be made. Accordingly, the recombinase allows the formation of the two expression cassettes employed in the two-component lethality system of the present invention. Other recombinase systems include the *Saccharomyces cervisiae* FLP/FRT, lambda att/Int, R recombinase of *Zygosaccharomyces rouxii*, and Mu Gin recombinase. Alternatively, one of the polynucleotides encoding a non-lethal peptide of the present invention could be located on a transposable element such as Ds from maize which could be excised by crossing to a line carrying a transposase (see, e.g., Carroll et al. *Genetics* 139:407–420 (1995)).

Using a recombinase system, two alternative alleles at one locus can be created encoding each one of the polypeptides of the present invention which, when homozygous, yield alternate sublines (e.g., sublines $A_1$ and $A_2$). Crossing of sublines $A_1$ and $A_2$ yield the heterozygote line, A. Since the alternate alleles of line A are at the same locus they will segregate away from each other upon crossing the line A heterozygote with a line which is absent either of these alleles, line B. The resulting hybrids will have only one functional expression cassette of the multi-component system per cell and, consequently, these cells will not yield a desired lethal or beneficial result (e.g., the male sterile line A described above will be 100% male fertile).

For example, sublines $A_1$ and $A_2$, each having one expression cassette of the two-component system, can be created using a recombinase system as described above, preferably the cre/lox system. The initial transformant will have a first polynucleotide, often encoding a first polypeptide, operably linked to a first promoter and inserted in opposite orientation between a second promoter which drives expression of a second polypeptide.

Lox sites are placed in the same orientation on both sides of the second expression cassette insert. When made homozygous (via any number of standard breeding) this will yield subline $A_1$. The first polynucleotide in this $A_1$ construct is not expressed since an insert is present between the first promoter and the polynucleotide encoding the first polynucleotide.

Subline $A_2$ is created by crossing line $A_1$ to a line carrying a recombinase which recognizes the recombination sites (e.g., the lox sites) and excises the intervening sequence allowing the first promoter to drive expression of the first polynucleotide to which it is operably linked. When made homozygous by breeding methods well known to those of skill in the art, this will be used as line $A_2$. Hybrid line A is formed by crossing sublines $A_1$ and $A_2$ to yield a plant comprising a functional multi-component system of the present invention.

In some embodiments a tet operator-Ms polynucleotide is inserted in opposite orientation between a tapetal-specific promoter such as TA29 and the tet repressor/VP16 (Act) activator. Lox sites are placed in the same orientation on both sides of these first promoter-first polynucleotide inserts. In the homozygous subline of this construct, $A_1$ the regulatory protein Act) is not expressed since the tet operator-Ms gene is present between the TA29 and Act (the regulatory protein). Subline $A_2$, which lacks the insert as a result of cre, expresses Act, the activator of the tet operator. Crossing of $A_1$ to homozygous subline $A_2$ results in expression of Ms and results in 100% male sterile hybrids.

In other embodiments, a pMon-Avr9 gene is flanked by lox sites and inserted in opposite orientation between a tapetal-specific promoter such as TA29 and Cf9. In this construct, only the pMon-Avr9 gene will be expressed. Another subline is created in which the insert is removed by a recombinase and the TA29 promoter drives expression of Cf9. Crossing of these two lines results in a hybrid which is male sterile due to the joint expression of Avr9 and Cf9 in tapetal cells.

Promoters

The promoters employed in the expression cassettes of the present invention can be chosen to function in identical sets of tissue types simultaneously, or at different stages of development or of the cell cycle. However, the individual promoters are generally chosen such that they will function in multiple, different, and overlapping subsets of cells. Accordingly, the promoters of the present invention typically have "different but overlapping specificities" The overlap of these different subsets is that collection of cells where all expression cassettes of the multi-component system are present and functional. The presence in a cell of all of the complete set of functional expression cassettes of the multi-component system will result in a desired effect on the organism. Thus, for example, a single functional expression cassette within a cell yields a non-lethal/non-inhibitory phenotype. However, the presence of both functional expression cassettes in the same cell yields the inhibitory or lethal phenotype.

A very wide range of promoters can be used with the multi-component system of the present invention. Methods for identifying promoters with a particular expression pattern, in terms of, e.g., tissue type, cell type, stage of development, and/or environmental conditions, are well known in the art. A typical step in promoter isolation methods is identification of gene products that are expressed with some degree of specificity in the target tissue. Amongst the range of methodologies are: differential hybridization to cDNA libraries; subtractive hybridization; differential display; differential 2-D gel electrophoresis; isolation of proteins known to be expressed with some specificity in the target tissue. Such methods are well known to those of skill in the art.

For the protein-based methods, it is necessary to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. If the cell lethality function is only formed upon association of two different gene products, then it is only necessary to identify two promoters with activity in the desired tissue or condition but that do not have activity in any other common tissue.

Once promoter and/or gene sequences are known, a region of suitable size is selected from the genomic DNA that is 5' to the transcriptional start, or the translational start site, and such sequences are then linked to a partial coding sequence as described above. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a partial coding sequence.

To identify the promoters, the 5' portions of the clones described here are analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions –80 to –100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). If proper polypeptide expression is desired, a polyadenylation region should be included. The polyadenylation region can be derived from the 3' end of a natural gene, from a variety of other plant genes, or from T-DNA.

Modification of the promoter characterized as described herein can be done using any of a number of methods well known in the art. For example, specific enhancer sequences can be added to the promoter to increase the expression level or to modify the expression pattern. Further, an intron sequence can be added to the 5' untranslated region or the coding sequence of the partial coding sequence to increase the amount of the mature message that accumulates in the cytosol.

Promoters of the present invention include tapetal-specific promoters TA29 from tobacco (Mariani et al., *Nature* 347:737–41 (1990)), 127a, 108, and 92b from tomato (Chen & Smith, *Plant Physiol.* 101: 1413–19 (1993); Aguirre & Smith, *Plant Mol. Biol.* 23:477–87 (1993)), and A6 and A9 from Brassica (Wyatt et al., *Plant Mol. Biol.* 19:611–22 (1992)). Anther-specific promoters could also be used such as ones isolated by Twell et al., *Mol. Gen. Genet.* 217:240–45 (1991) or Scott et al., *Plant Mol. Biol.* 17:195–207 (1991). Seed coat specific promoters, such as the pT218 promoter (Fobert et al., *The Plant Journal* 6:567–77 (1994)) or the pWM403 promoter could also be used in the present invention. Tissue-specific promoters for a range of different tissues have been identified, including roots, sepals, petals, and vascular elements. In addition, promoters induced upon pathogen infection have been identified, such as the prp-1 promoter (Strittmatter et al., *Bio/Technology* 13:1085–90 (1995)). Promoters induced in specialized nematode feeding structures have been identified (disclosed in patent applications WO 92/21757, WO 93/10251, WO 93/18170, WO 94/10320, WO 94/17194). Another useful promoter is the tet artificial promoter comprising at least one tet operators and a TATA-box (Weinman et al., 1994). This promoter is transcriptionally activated by an activator made by fusing the tet repressor, which recognizes the tet operator, to a eukaryotic activation domain.

Preferably, the activation domain is the viron protein 16 (VP16) activation domain from Herpes simplex virus. This tet repressor/VP16 activator fusion (also referred herein as "Act") has activates transcription in plants. Other operator recognition systems that can be used include lacR/O, GAL4, and 434R/O. Other activator domains which can be employed in the present invention include the acid domains from Vp1, ABI3, PvAlf, HAP4, and GCN4. Non-acidic activator domains can also be used, such as proline-rich domain, serine/threonine-rich domains, and glutamine-rich domains.

Lethal and Beneficial Effects

Each expression cassette of the present invention is individually functional but the product of each cassette alone does not provide the desired effect. It takes the combination of all transcripts (typically translated into polypeptides) from the individual expression cassettes to result in the desired phenotype. Such transcripts are individually are non-functional. For example, lethal or inhibitory transcripts can provide sense or antisense suppression, or lethal or inhibitory transcripts can be translated into a prozyme which is activated upon processing by a specific protease which is the product of the other expression cassette.

The expression cassettes of the present invention can also jointly provide a beneficial effect to a cell. Thus, individually each expression cassette encodes a transcript which is non-functional or encodes a non-functional polypeptide. However, the presence of both transcripts or their encoded products in a cell (e.g., both monomers of a heterodimeric protein) provides a desired function to the cell. Thus, the present invention provides lethal as well as restorative or therapeutic benefits to desired cells.

A. Polypeptides

Polypeptides of the present invention can consist of separate functional proteins from distinct loci, or the polypeptides can be derived from overlapping or non-overlapping subsequences of a single functional protein which provides for the desired phenotype when co-expressed in a cell. Additionally polypeptides of the present invention can consist of separate monomers of a lethal dimeric protein. In some embodiments the polypeptides will be a prozyme and the specific protease which processes the prozyme and renders it inhibitory or lethal.

In some embodiments, the multi-component system of the present invention is a two-component system. The two-component (two peptide) system, in which the two components are derived from a one-component (single protein) can generally be derived from any single protein that has a cell-lethal or inhibitory function (depending only upon the protein folding constraints of the initial protein). Typically, the two peptides are from non-overlapping or minimally overlapping (e.g., 50, 35, 20, 15, 10, 5 or less) subsequences from a single inhibitory or cytotoxic protein. The peptides produced reassociate in the target cell reconstituting the function of the single peptide from which the 2 partial peptides are derived.

The secondary and tertiary structure of a host of proteins and the processes of protein folding are known to those of skill and provide the basis for designing two-component peptide systems from a single protein. The 2 peptides will relate to the starting protein as 1) unmodified peptides that comprise the entire original protein, with the addition of a methionine or the conservative replacement of an amino acid with a methionine at the point of separation of the 2 peptides; 2) modified peptides as in (1) with the additional replacement of some amino acids by other amino acids designed to enhance the stability of the peptides and reassociated peptide complex; 3) modified peptides that comprise less than the full protein in toto; 4) peptides that are derived from only a portion of the original protein, where the portion of the original protein encodes a suitable function.

The design of non-functional polynucleotides or their encoded polypeptides can be achieved by a number approaches well known to the skilled artisan. In the instant invention, these polynucleotides or polypeptides, when co-expressed in a cell, can confer lethality or some other desired function. These peptide subsequences, taken together, can be related to the original peptide as comprising the total protein sequence of the original functional protein, or as comprising a portion of the total protein sequence only. To ensure that sufficient temperature stability is retained in the now dimeric active protein, it may be necessary to incorporate specific amino acid changes into the partial coding sequences. The amino acid changes can be determined by examination of the original protein and the known amino acid interactions based on the protein structure as revealed through a range of physical techniques. In addition, the amino acid changes can be determined by random mutagenesis and screening of a combinatorial library of protein products. Alternatively, the amino acid changes can be determined by completely random mutagenesis and selection, using chemical treatments, PCR-induced mutagenesis, or other similar mutagenic treatments known to those skilled in the art.

The partial coding sequences derived from the original protein coding sequences is selected to retain activity of the reconstituted protein as well as a suitable level of stability with respect to environmental perturbations such as temperature changes. Several general routes can be taken to determining effective partial coding sequences.

i. Partial Proteolysis

A number of proteins have been separated into distinct, resolvable domains through partial proteolysis. This is a rapid way to determine suitable coding sequences for the two non-functional polynucleotides or polypeptides of the instant invention. For example, pancreatic ribonuclease A can be cleaned by subtilisin between residues 20 and 21, yielding a large and a small peptide, neither of which retains any activity, as essential catalytic residues are present in each peptide fragment. When the two peptides are mixed, the small peptide binds to the larger fragment and activity is reconstituted. In another example, staphylococcal nuclease can be resolved into three peptide fragments following partial proteolysis. Proteases initially cleave an intact protein at exposed residues, often ones that are part of exposed loops not involved in specific domains. Following partial proteolysis and analysis of the resulting peptide fragments by polyacrylamide gel electrophoresis to confirm that a simple digestion resulted, residual activity is evaluated. If activity is retained, the peptides are separated to determine whether neither peptide retains activity separately, and subsequently whether activity can be reconstituted upon remilling. Sequencing of the amino and carboxy termini of the two (or more) fragments reveals how to engineer the partial coding sequences in the instant invention.

ii. Sequence Conservation-based Design

In situations where a number of sequences are available for proteins with the same function (e.g., subtilisin family proteins; colicin family proteins; ribonuclease family proteins), it is possible to identify regions that are not well conserved in all proteins. In combination with predictive analysis of secondary structure, it is possible to identify regions of the protein that are good candidates for separation into separate peptides. Such regions retain unaltered principal secondary structural features, such as alpha helices and beta-sheets. Within such regions, a number of possible replacement and coding sequence variants can be tested using an assay either for protein function in vitro, or for function, or for in vivo lethality.

iii. Structure-based Design

When a three-dimensional structure is available, from x-ray crystallography, NMR spectroscopy, etc., a more precise determination of candidate regions that would comprise the partial peptides of a single functional protein is possible. Analysis of the interactions between individual amino acids in a three-dimensional structure reveals sub-domains of the original protein that have the potential to be separated and yet to bind to each other, and which sub-domains are likely to be non-functional when present separately. Additionally, analysis of these interactions reveals which amino acids, located between suitable sub-domains, are not involved in specific interactions with other amino acids in a way that would permit replacement with a methionine residue. Such an analysis is aided by additional sequence data for proteins with a high proportion of sequence relatedness to the starting protein. This provides additional evidence concerning residues that can be replaced with a methionine residue.

Exemplary polypeptides of the present invention include ribonucleases such as barnase (Mauguen et al., *Nature* 297:162–64 (1982)), binase (Pavlovsky et al., *FEBS Lett.* 162:167–70 (1983)), Ribonuclease T1 (Fujii et al., *Biosci. Biotechnol. Biochem.* 59:1869–1874 (1995)), nucleases such as colicin E9 (Wallis et al., *Eur. J. Biochem* 220:447–54 (1994)) or BamHI (Newman et al., *Science* 269:656–63 (1995)), and proteases such as subtilisin BPN' (Eder et al., *J. Mol. Biol.* 233:293–304) or other members of the subtilisin family. In some embodiments, these polypeptides are used to yield male sterility when co-expressed in tapetal tissue. Other polypeptides for creating cell toxicity or inhibition include those which produce toxic substances, disrupt cell function, suppress genes required by the cell (such as by using anti-sense, sense suppression, or ribozymes), and disruption of mitochondrial function. In particularly preferred embodiments, the polypeptide is derived from a separate subsequence of a ribonuclease such as barnase. For barnase, the minimal length of each polypeptide is at least 20 amino acids. Generally, the extent of overlap of barnase polypeptides will be no more than 5 amino acids.

The enzyme barnase is a well-studied cell lethality function that has already been shown to be cell-autonomous, independent of other cellular functions, and very sensitive. Barnase expression has been shown to inhibit cell growth and development in specific plant tissues. The mature barnase protein consists of a 110 amino acid polypeptide. It has been shown in in vitro studies that amino acid 37 of the mature protein can be converted from a valine to a methionine with good retention of ribonuclease activity. Sancho & Fersht, *J. Mol.Biol.* 224:741–47 (1992). It has also been shown that cyanogen bromide treatment cleaves the protein into a 36 amino acid peptide and a 74 amino acid peptide and that neither peptide retains any activity. Further, at least 30% of normal activity is reconstituted when the two peptides are mixed in vitro. Sancho & Fersht, supra.

A particularly preferred embodiment is to produce the following two partial barnase coding subsequences via PCR amplification using a barnase gene as template and 1) primers designed to introduce a methionine codon at position 1 of the mature protein coding sequence and a stop codon after position 36 of the mature protein sequence, and 2) primers designed to introduce a methionine codon at position 37 of the mature protein coding sequence while leaving the end of the mature protein coding sequence intact. The two partial coding sequences can then be manipulated further to produce expression cassettes, using, for example, a promoter, a 5' untranslated region, a 3' untranslated region, and a polyadenylation signal. The two expression cassettes can be designed to create two-component lethality systems that could be used to create a range of useful traits. Another exemplary two-component polypeptide system is the use of the Avr9 elicitor polypeptide from *Cladosporium fulvum* and the corresponding resistance gene, Cf9 from *Lycopersicon esculentum*. A hypersensitive response is elicited in cells expressing both Avr9 and Cf9 resulting in cell death.

Means to assay for eukaryotic cell cytoxicity or inhibition produced by two peptide fragments of a single protein are well known in the art. For example, to determine whether the partial peptides designed as indicated above can be expressed separately without activity, but can be expressed together to give activity, enzymatic activity can be assayed directly on cell extracts containing the expressed peptides or in purified preparations of the peptides. Further, eukaryotic cell cytotoxicity or inhibition can be assayed using a range of indicators for cell function. In one preferred method, the expression cassettes can be introduced to cells along with an expression cassette that produces an easily assayed function, such as the beta-glucuronidase protein (Jefferson et al., *EMBO J.* 6:3901–3907 (1987)) or firefly luciferase (De Wet et al., *Mol. Cell. Biol.* 7:725–37 (1987)). If expression of the expression cassettes together is cytotoxic, then the amount of the reporter activity detected will be reduced compared with the activity detected when an expression cassette is introduced separately into a eukaryotic cell. Additionally, for example, two peptides derived from non-overlapping or minimally overlapping subsequences from a single inhibitory or cytotoxic protein such as a ribonuclease can be assayed for ribonucleolytic activity in vitro.

The peptides of the invention may also be modified according to standard methodology to produce polypeptides with, either separately or in combination, e.g., enhanced thermal stability, enhanced subunit association, enhanced activity at lower concentrations and the like. These peptide can also be modified to produce conservatively modified variants. The modification of the polypeptides can be achieved, e.g., by techniques known to those skilled in the art such as random or site-specific mutagenesis of the nucleic acids that encode the polypeptides. Using such methods of mutagenesis, genetically modified peptides are then assayed for reconstitution of activity in vivo. Activity at lower concentrations or at higher temperatures is measured by comparing the genetically modified and the original peptides.

For example, the two barnase components described above are modified separately in a way that has been shown to enhance stability of the intact barnase protein (see Example 9). The modifications selected are based on the work of Serrano et al., *J. Mol. Biol.* 233:305–12 (1993), who compared the thermodynamic stability of barnase with a related protein, binase, obtained from *Bacillus intermedius*. Binase has the same amino acid sequence as barnase at all but 18 of the 110 amino acid positions. Serrano et al. replaced each of the barnase amino acids with a different amino acid at positions in which the proteins differed, and measured the change in thermodynamic stability induced by the amino acid change. Enzyme activity was also measured for a subset of the mutagenized barnase forms. In this way, specific amino acid changes that enhanced stability, but had little effect on enzyme activity were identified. In particular, for the amino-terminal peptide, the glutamine at position 15 of the mature barnase protein was replaced by isoleucine, and the threonine at position 16 was replaced by arginine; for the carboxy-terminal peptide, the glycine at position 65 was replaced with a serine, and the lysine at position 108 was replaced with an arginine. These changes lead to improved function when the two modified peptides are expressed in place of the original peptides. These specific changes exemplify the type of amino acid changes that are possible; those experienced in the art will recognize that other such amino acid replacements can lead to enhanced function of the two-component system. Such changes could be ones that enhance the overall activity (Vmax) of the dimeric enzyme rather than the stability of the dimeric enzyme.

B. Transcripts

In addition to polypeptides, the transcription products of number of DNA constructs can be used to suppress expression of endogenous plant genes and yield a beneficial or lethal result to the cell. These include cassettes which provide sense or antisense suppression, or ribozymes which, in combination with a second expression cassette, inhibit or kill the cell. Anti-sense RNA inhibition of gene expression has been shown; see, e.g., Sheehy et al., *Proc. Nat. Acad. Sci. USA* 85:8805–8809 (1988), and Hiatt et al., U.S. Pat. No. 4,801,340. For examples of the use of sense suppression to modulate expression of endogenous genes see, Napoli et al., *The Plant Cell* 2:279–289 (1990), and U.S. Pat. No. 5,034,323.

Catalytic RNA molecules or ribozymes can also be used to inhibit gene expression. For example, in some embodiments a beneficial or lethal ribozyme can be transcribed upon induction by a polypeptide expressed from a second expression cassette (e.g., tet repressor/VP16 activator fusion polypeptide). It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. A general design and use of target RNA-specific ribozymes is described in Haseloff et al. *Nature,* 334:585–591 (1988).

For antisense suppression or sense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

C. Regeneration

Transformed plant cells which are derived by any number of transformation techniques can be cultured to regenerate a whole plant which possesses the transformed genotype and thus the desired expression cassette. Such regeneration techniques rely on manipulation of certain phytohormones in a tissue culture growth medium, typically relying on a biocide and/or herbicide marker which has been introduced together with the polynucleotide encoding a desired polypeptide. Plant regeneration from cultured protoplasts is described in Evans et al., *Protoplasts Isolation and Culture, Handbook of Plant Cell Culture,* pp. 124–176 (1983); and Binding, *Regeneration of Plants, Plant Protoplasts,* pp. 21–73 (1985). Regeneration can also be obtained from plant callus, explants, organs, or parts thereof. Such regeneration techniques are described generally in Klee et al., *Ann. Rev. of Plant Phys.* 38:467–486 (1987).

In some embodiments of the present invention, the expression cassettes encoding each component of the two or more component system are either introduced into a single cell by cotransformation of cells with each of the two expression cassettes, or by sequential transformation of cells with the two expression cassettes. When two promoters with overlapping specificity are used, cell inhibition or lethality will result in only the target tissue in which both promoters are sufficiently active.

In other embodiments the expression cassettes are introduced into different cells by transformation. Whole organisms are regenerated from the separated transformed cells, and then a hybrid organism is produced by crossing the individual organisms. In this way, the original whole organisms, each carrying a single expression cassette show no cell inhibition or lethality. However, the hybrid organism resulting from the cross will have both expression cassettes in the same cell, and will express cell inhibitory function or lethality in a manner dependent upon the expression patterns of the chosen promoters.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

D. Target Cell Types

As the present invention can be used to eliminate particular cells or tissue types, a number of desired traits can thus be introduced into a plant. For example, in order to produce seedless fruit of a seed propagated crop, inbred lines are made, each comprising one of the two expression cassettes whose joint expression leads to inhibition or death of the cell. For example, each expression cassette can express a non-lethal polypeptide from a seed-specific promoter. When the inbred lines are crossed, the resulting hybrid, which would be used in commercial production of a seedless fruit, carries both components that combine to block seed development in the fruit of the hybrid plant. Because the inbred lines do not carry a functional lethality gene, each line can be maintained in a homozygous condition for one of the expression cassettes.

To produce male sterility, each of the two polynucleotides is operably linked to a promoter functional in tapetal cells or pollen cells, either using the same promoter with each polynucleotide or different promoters. Inbred lines are maintained, each comprising one of the polynucleotides in homozygous condition. When the inbred lines are crossed, the resulting hybrid carries both partial genes and is male-sterile. If the two inbreds are the same line, except for the partial barnase polypeptide, then the resulting "hybrid" is a male-sterile inbred that can be used in a hybrid breeding strategy.

To produce female sterility, each of the polynucleotide sequences is operably linked with a promoter expressed in stigmatic tissues, tissues of the transmitting tract, ovule tissues, or other tissues essential for female fertility. Inbred lines are maintained, each comprising one of the two polynucleotides in homozygous condition. When the inbred lines are crossed, the resulting hybrid carries both polynucleotides and is female-sterile. If the two inbreds are the same line, except for the partial barnase gene, then the resulting "hybrid" is a female-sterile inbred that can be used in a hybrid breeding strategy.

Disease resistance in plants can be mediated by a hypersensitive response in which cells infected by a pathogen are killed to prevent further spread of the pathogen. Using promoters induced by pathogen attack and a two-component system of the present invention, a synthetic hypersensitive response can be created. For example, tolerance to root knot or cyst nematodes can be mediated by eliminating the giant cells or specialized feeder cells these pests require for continued growth and multiplication in plant roots. Using promoters induced in the giant cells or specialized feeder cells in combination with a two-component system of the present invention, these specialized root cells can be eliminated.

Hybrid seeds comprising both expression cassettes of the multi-component system are typically produced in a maintainer field using sub-lines $A_1$ and $A_2$. These sublines comprise one or the other of the two expression cassettes of the two-component system which when functional in the same cell lead to cell inhibition or cell death. Both sublines $A_1$ and $A_2$ are fertile since each carries one expression cassette of the two-component system of the invention. Upon crossing to produce line A, cell death or inhibition is initiated in the cells where both expression cassettes are functional. In some embodiments, one subline will comprise an expression cassette comprising a polynucleotide from the *Cladosporium fulvum Avr9* avirulence gene operably linked to a tapetal-specific promoter such as pMon. In the other subline the tomato Cf9 gene (the corresponding tomato resistance gene) is operably linked to a second tapetal-specific promoter, TA29. Both sublines are male fertile since the Avr9 and Cf9 polypeptides individually do not confer cell death. However, when these sublines are crossed they yield a line in which a hypersensitive response is initiated in the tapetum resulting in cell death. Hammond-Kosack et al., *PNAS* 91:10445–10449 (1994); Jones et al., *Science* 266:789–793 (1994). Tapetal cell death will confer male-sterility without adversely affecting other organs. In the hybrid seed production field, the male sterile line A can be crossed to any line B to produce hybrid seeds.

In some embodiments, one subline has a dominant male sterile gene (Ms) with an artificial promoter comprising at least one tet operator and a TATA-box. In this condition the male sterile gene is not transcribed and the subline is male fertile. The corresponding subline has a tapetal-specific promoter driving the expression of a chimeric transcriptional activator. Preferably, this chimeric transcriptional activator will be Act. Weinmann et al., *The Plant Journal* 5(4):559–569 (1994). The line produced from crossing the sublines will be male sterile since it contains both the transcriptional activator (Act), which is expressed specifically in the tapetum, and the tet operator-Ms gene. Tapetal-specific expression of Ms genes such as ribonucleases (e.g., Barnase), or premature expression of β-1,3 glucanases in the tapetum, have been shown to produce male sterility. In the hybrid seed production field, the male sterile line A can be crossed to any line B to produce hybrid seeds.

Mammalian Cellular Transfection and Gene Therapy

The present invention further provides packageable DNA or RNA (nucleic acid) constructs for a multi-component lethality or inhibitory system as described more fully above. The various constructs employed in gene therapy methods can be had by reference to the compositions and methods described earlier. Thus the constructs of the invention can be used to target specific mammalian cells. The packageable nucleic acid constructs allow for the transfection of eukaryotic cells in vivo or ex vivo. Generally, the eukaryotic cells are mammalian hosts, such as mice, rodents, primates, and humans. The packageable nucleic acids of the invention can be inserted into any of a number of well known vectors for the transfection of target cells and organisms as described below. Cells are transfected with a expression cassette comprising a polynucleotide operably linked to a promoter functional in the cell or in a cell of a later developmental stage. Cells transfected all of the functional expression cassettes of the multi-component lethality system will inhibit cell growth (i.e., the cell doesn't enter the cell cycle) or kill the cell. However, those of skill in the art will recognize that the multi-component system of the present invention can be modified to provide a therapeutic effect upon transfection with all functional expression cassettes of the multi-component system; such embodiments can employ any polypeptide which produces a desirable effect.

Preferred embodiments of the present invention is targeted killing of cancerous cells. A cell capable of causing cancerous growth in a mammal is altered in multiple ways via mutation from a mammalian cell that is not capable of causing cancerous growth. It is known in the art that defects occur in the control of cell growth control networks, in the control of telomere length and in the control of contact-mediated cell growth inhibition. Although there are common themes and mechanisms underlying causation of specific cancers, a wide range of genes have been identified as oncogenic when their expression is altered or their function is altered. Certain genes are often expressed in cancerous cells which are normally not expressed in the mature cells of an intact organism. The promoters of such genes can be used in the instant invention to create a two-component system that will form a lethal function in a cancerous cell, but not in a cell under normal controls for the cell cycle, contact inhibition and telomere formation. Typical promoters would be selected from a group that includes, but is not limited to, a telomerase promoter, or a promoter under the control of myc genes. The polynucleotides of the two-component system can be delivered to cancerous cells via disarmed human viruses, liposome fusion, or other method.

The term "transfected" includes reference to the introduction of a nucleic acid into a eukaryotic cell where the nucleic acid can be incorporated into the genome of the cell (i.e., chromosome, plasmid, or mitochondrial DNA), converted into an autonomous replicon, or transiently expressed (e.g., transfected mRNA). The nucleic acids are transfected into cells, ex vivo or in vivo, through the interaction of the vector and the target cell. Vectors which target distinct cell types are known in the art. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Mulligan, *Science* 926–932 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler and Böhm eds., 1995); and Yu et al., *Gene Therapy* 1:13–26 (1994).

Delivery of the gene or genetic material into the cell is the first critical step in gene therapy treatment of disease. A variety of methods for delivering and expressing a nucleic acid within a mammalian cell are known to those of ordinary skill in the art. Such methods include, for example liposome-based gene delivery (WO 93/24640; Mannino Gould-Fogerite, *BioTechniques* 6(7):682–691 (1988); U.S. Pat No. 5,279,833; WO 91/06309; Felgner et al., *Proc. Natl. Acad. Sci. USA* 84:7413–7414 (1987); and Budker et al., *Nature Biotechnology*, 14(6):760–764 (1996)). Other methods known to the skilled artisan include electroporation (U.S. Pat. Nos. 5,545,130, 4,970,154, 5,098,843, and 5,128,257), direct gene transfer, cell fusion, precipitation methods, particle bombardment, and receptor-mediated uptake (U.S. Pat. Nos. 5,547,932, 5,525,503, 5,547,932, and 5,460,831). See also, U.S. Pat. No. 5,399,346.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al., *J. Virol.* 66(5):2731–2739 (1992); Johann et al., *J. Virol.* 66(5): 1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700, and Rosenburg & Fauci, in *Fundamental Immunology, Third Edition* (Paul ed., 1993) and the references cited therein, and Yu et al., *Gene Therapy* (1994) supra).

AAV-based vectors are also used to transduce cells with target nucleic acids, e.g., in the in vitro production of nucleic acids and polypeptides, and in vivo and ex vivo gene therapy procedures. See, West et al., *Virology* 160:38–47 (1987); U.S. Pat. No. 4,797,368; WO 93/24641; Kotin, *Human Gene Therapy* 5:793–801 (1994); Muzyczka, *J. Clin. Invst.* 94:1351 (1994) and Samulski (supra) for an overview of AAV vectors. Construction of recombinant AAV vectors are described in a number of publications, including Lebkowski, U.S. Pat. No. 5,173,414; Tratschin et al., *Mol. Cell. Biol.* 5(11):3251–3260 (1985); Tratschin et al., *Mol. Cell. Biol.* 4:2072–2081 (1984); Hermonat & Muzyczka, *Proc. Natl. Acad. Sci. USA* 81:6466–6470 (1984); and Samulski et al., *J. Virol.* 63:03822–3828 (1989). Cell lines that can be transfected by rAAV include those described in Lebkowski et al., *Mol. Cell. Biol.* 8:3988–3996 (1988).

A. Ex vivo Transfection of Cells

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an expression cassette of the present invention (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique, third edition* (1994)) and the references cited therein for a discussion of how to isolate and culture cells from patients).

In one particularly preferred embodiment, stem cells are used in ex-vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34$^+$ cells in vitro into clinically important immune cell types using cytokines such a GM-CSF, IFN-γ and TNF-α are known (see, Inaba et al., *J. Exp. Med.* 176:1693–1702 (1992)).

In mice, stem cells are isolated from bone marrow cells by panning the bone marrow cells with antibodies which bind unwanted cells, such as CD4$^+$ and CD8$^+$ (T cells), CD45$^+$ (panB cells), GR-1 (granulocytes), and Ia$^d$ (differentiated antigen presenting cells). For an example of this protocol see, Inaba et al., *J. Exp. Med.* 176:1693–1702 (1992). Human hematopoietic progenitor and stem cells are characterized by the presence of a CD34 surface membrane antigen. This antigen is used for purification, e.g., on affinity columns which bind CD34. See, Ho et al., *Stem Cells* 13 (suppl. 3):100–105 (1995). See also, Brenner, *Journal of*

*Hematotherapy* 2:7–17 (1993). In another embodiment, hematopoietic stem cells are isolated from fetal cord blood. Yu et al., *Proc. Natl. Acad. Sci. USA* 92:699–703 (1995) describe a preferred method of transducing CD34⁺ cells from human fetal cord blood using retroviral vectors.

B. In vivo Transfection

Vectors (e.g., retroviruses, adenoviruses, liposomes, etc.) containing therapeutic nucleic acids can be administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampules and vials.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered, the physician evaluates circulating plasma levels of the vector, vector toxicities, progression of the disease, and the production of anti-vector antibodies. In general, the dose equivalent of a naked nucleic acid from a vector is from about 1 $\mu$g to 100 $\mu$g for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the LD-50 of the transduced cell type, and the side-effects of the cell type at various concentrations, as applied to the mass and overall health of the patient. Administration can be accomplished via single or divided doses.

Transduced cells are prepared for reinfusion according to established methods. See, Abrahamsen et al., *J. Clin. Apheresis,* 6:48–53 (1991); Carter et al., *J. Clin. Apheresis* 4:113–117 (1988); Aebersold et al., *J. Immunol. Meth.* 112:1–7 (1988); Muul et al., *J. Immunol. Methods* 101: 171–181 (1987) and Carter et al., *Transfusion* 27:362–365 (1987). After a period of about 2–4 weeks in culture, the cells should number between 1×10⁸ and 1×10¹². In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

Treatment of Non-Mammalian Organisms

While the two or more component lethality system of the present invention is preferably employed with multicellular eukaryotic organisms such as a mammal or plant, it is also applicable to any organism, as cell inhibitory or lethality functions (e.g., ribonucleases, deoxyribonucleases, proteases, toxins) are known that effect all types of cells. The principles of protein structure and protein folding apply universally in living cells, and thus multi-component systems will function in cells of all types. In addition, a range of promoters with various expression patterns are known in the art for prokaryotic and non-plant eukaryotic cells. The combination of specifically expressed promoters with a two-component system is therefore general.

Accordingly, for example, a two-component lethality system can also be applied to prokaryotic organisms. When it is desirable to kill or inhibit the growth of bacterial cells growing within a mammalian organism, a two or more component system can be delivered to the bacterial cells specifically using specialized bacteriophage. In this case, a single promoter that is highly expressed in the target bacterial cell but without activity in the host organism or other beneficial bacterial cells, can be used with each partial coding sequence, and the two genes delivered to the target bacterial cells in the genome of a specialized bacteriophage. As will be clear to the skilled artisan, the system can be expanded to utilize greater than two components.

Although the present invention has been described in some detail by way of illustration and example for purposes of clarity of understanding, it will be obvious that certain changes and modifications may be practiced within the scope of the appended claims.

EXAMPLE 1

Example 1 describes the synthesis of partial barnase genes using a constitutive promoter.

The complete barnase coding sequence, from *B. amyloliquifaciens*, is available from GenBank under accession number M14442. Paddon & Hartley, *Gene* 40:231–239 (1986); Paddon et al., *J. Bacteriol.* 171:1185–1187 (1989). Pro I barnase is cleaved to form pro II barnase (positions 391–735) after which it is cleaved again to form the mature peptide consisting of 110 amino acids. To produce two coding sequences that would encode completely nonfunctional peptides which would combine to give functional barnase, two pairs of PCR primers were synthesized. PCR amplifications were done according to manufacturer's recommended conditions, using Taq DNA polymerase, each pair of primers separately, and chromosomal DNA isolated from *Bacillus amyloliquifaciens* strain ATCC #23842. Bacterial DNA was isolated using standard methods.

The resulting fragments comprising the 5' partial coding sequence (bn5) and the 3' partial coding sequence (bn3), synthesized to have an NcoI site at the 5' end and an XbaI site at the 3' end of each fragment were gel purified. After digestions with NcoI and XbaI, each fragment was cloned into plasmid pNG5104, with the coding sequence of the β-glucuronidase (uidA) gene removed by NcoI-XbaI digestion and gel purification of the resulting large fragment. The resulting genes have each partial coding sequence operably linked to the SpMas promoter (Gelving et al., 1995) and to the 3' polyadenylation region of the octopine synthase gene. The size of the inserted fragments was verified by gel electrophoresis, and at least two clones for each of the 5' genes (SpMas-bn5) and the 3' genes (SpMas-bn3) was selected for sequence analysis. The sequences were confirmed for each of the genes, and the resulting plasmids were designated pER4013 (SpMas-bn5) and pER4022 (SpMas-bn3). The bn5 coding sequence encodes a peptide with a methionine added prior to the amino-terminal alanine of the mature barnase protein, and with a carboxy-terminal tryptophan (mature protein position 35). The bn3 coding sequence encodes a peptide with the initiation methionine in place of the valine of the barnase mature protein position 36 and with the correct carboxy-terminal arginine (mature protein position 110).

EXAMPLE 2

Example 2 describes biollistics assay for the reconstitution of a lethal function in plant cells.

Reconstitution of cell lethality was assayed by bombarding plant leaves with a mixture of pER4013 and pER4022 phagemid DNAs, along with DNA of phagemid pLVC320, which comprises a SpMas-LUC chimeric gene. As controls, pER4013 and pLVC320 were delivered biollistically, and pER4022 and pLVC320 were delivered biollistically. The plasmid DNA's were prepared as single stranded, circular molecules using the M13 origin of replications in these phagemids. After determining DNA concentration by spectrophotometry, the concentration of each plasmid was adjusted to 400 µg/µl in 10 mM Tris-1 mM EDTA, pH 8.0.

The plasmid DNA's were mixed according to standard methods and coated onto tungsten particles by mixing 80 µl of each DNA mixture with 40 µl of M17 tungsten particles (100 mg/ml in sterile water), 40 µl of 100 mM spermidine, and 100 µl of 2.5 M CaCl2 in rapid succession. After mixing by vortexing, the particles were allowed to remain on ice for 5 min, after which the particles were collected by centrifugation in a microcentrifuge for 20 sec. The supernate was removed, and the particles suspended in 100 µl of 70% ethanol.

Bombardment was performed using a device based on the Particle Inflow Gun of Finer and his colleagues. Sterile tomato leaf disks, prepared with a no. 4 cork borer and placed on sterile GF/A filter disks on Murashige and Skoog medium without any plant hormones, were bombarded with 6 µl of a particle prep. The particle prep was pipetted onto the surface of the bottom half of a swinney filter unit. This was then attached to the upper half of a swinney filter unit that was attached to the Helium line at the top of the biollistic chamber. Using a pressure of 200 psi in a Helium tank, the prechamber was loaded with Helium. After drawing a pressure of 29 inches Hg in the biollistics chamber, the Helium gas in the prechamber was released, firing the particles onto the surface of the agar in a petri plate located 12 cm from the swinney unit. Leaf disks were incubated 16 hours at 22° C. prior to performing luciferase assays.

Luciferase assays were performed according to Promega, using S-adenosyl-methionine (SAM) as the energy source to prolong the burst of photon release. Plant leaf extracts were prepared in Cell Lysis Buffer, and then stored on ice. The assay tubes with 40 µl of assay solution including luciferin and SAM were preincubated at room temperature for 2 min. to 5 min. before initiating the reaction by addition of 10 µl of extract. After mixing, tubes were immediately transferred to Beckman scintillation counter LS6800, and light emission detected using the single photon counting program (special program number 6). Light emission is determined as photons (or counts) per minute (cpm), after subtracting background determined using 10 µL extract buffer in the reaction.

The luciferase assay results in Table 1 are reported as cpm/leaf disk. The combination of SpMas-bn5 with SpMas-bn3 results in a 84% reduction in luciferase activity compared with SpMas-bn5 alone and a reduction of 71% compared with SpMas-bn3 alone. This indicates reconstitution of cell lethal function by expression of the separate bn5 and bn3 peptides in the same cells. Similar results are reported in Tables 2–4.

TABLE 1

Luciferase activity recorded as cpm/leaf disk as described in example 2. Each construct introduced biolistically was introduced along with a luciferase reporter construct.

| Gene construct | bn5 alone | bn3 alone | bn3 + bn5 |
|---|---|---|---|
| shot 1 | 454,355 | 1,563,355 | 281,355 |
| shot 2 | 176,555 | 561,355 | 120,155 |
| shot 3 | 1,147,355 | 145,655 | 288,855 |
| shot 4 | 686,155 | 1,169,355 | 52,155 |
| shot 5 | 1,146,355 | 377,355 | 66,355 |
| shot 6 | 500,355 | 1,294,355 | 132,355 |
| shot 7 | 4,035,355 | 239,355 | 124,355 |
| shot 8 | 1,274,355 | 608,355 | 257,355 |
| average | 1,177,605 | 744,893 | 165,368 |

TABLE 2

Luciferase activity recorded as cpm/leaf disk and as the average for 8 leaf disks. Each construct introduced biolistically was introduced along with a luciferase reporter construct as described in example 2. Samples not measured for technical reasons are reported as "lost".

| Gene construct | bn5 alone | bn3 alone | bn3 + bn5 |
|---|---|---|---|
| shot 1 | 888,225 | 296,695 | 21,235 |
| shot 2 | 322,375 | 301,855 | 47,105 |
| shot 3 | 754,275 | 597,965 | 40,745 |
| shot 4 | 378,795 | 313,415 | 121,145 |
| shot 5 | lost | 1,353,735 | 250,905 |
| shot 6 | 652,065 | 3,120,605 | 463,765 |
| shot 7 | 232,505 | 521,875 | 285,625 |
| shot 8 | 431,625 | 398,445 | 390,765 |
| average | 522,838 | 863,074 | 202,661 |

TABLE 3

Luciferase activity recorded as cpm/leaf disk and as the average for 8 leaf disks. Each construct introduced biolistically was introduced along with a luciferase reporter construct as described in example 2.

| Gene construct | bn5 alone | bn3 alone | bn3 + bn5 |
|---|---|---|---|
| shot 1 | 597,940 | 363,740 | 203,760 |
| shot 2 | 2,446,650 | 503,250 | 408,980 |
| shot 3 | 278,710 | 2,209,780 | 944,780 |
| shot 4 | 575,950 | 1,012,100 | 115,940 |
| shot 5 | 708,800 | 7,888,740 | 44,530 |
| shot 6 | 890,410 | 7,569,830 | 230,250 |
| shot 7 | 1,015,610 | 1,207,308 | 153,570 |
| shot 8 | 279,350 | 2,612,020 | 723,220 |
| average | 849,178 | 2,920,855 | 353,129 |

TABLE 4

Luciferase activity recorded as cpm/leaf disk and as the average for 8 leaf disks. Each construct introduced biolistically was introduced along with a luciferase reporter construct as described in example 2. Samples not measured for technical reasons are reported as "lost".

| Gene construct | bn5 alone | bn3 alone | bn3 + bn5 |
|---|---|---|---|
| shot 1 | lost | 38,375 | 9,605 |
| shot 2 | 157,915 | 849,235 | 103,795 |
| shot 3 | 274,385 | 552,715 | 165,205 |
| shot 4 | 103,725 | 462,695 | 141,635 |
| shot 5 | 247,325 | 202,525 | 215,535 |
| shot 6 | 1,475,195 | 155,895 | 77,775 |
| shot 7 | 1,550,975 | 156,225 | 439,265 |
| shot 8 | 3,023,765 | 1,133,925 | 665,155 |
| average | 976,184 | 443,949 | 227,246 |

EXAMPLE 3

Example 3 describes tobacco lines expressing an amino-terminal barnase partial peptide and a carboxy-terminal barnase partial peptide under control of a strong constitutive promoter.

The SpMas-bn5 gene in pER4013 is recloned as a PvuII fragment into the SmaI site of T-DNA vector pWTT2200, which has an nptII gene as the selectable marker to confer resistance to kanamycin or G418. The SpMas-bn3 gene in pER4022 is recloned as a PvuII fragment into the SmaI site of T-DNA vector pNG5185, which has an ALS gene as the selectable marker to confer resistance to chlorsulfuron.

Each construct, along with vector only controls, is introduced separately into *Nicotiana tobaccum* cultivar petite Havana using standard leaf disk transformation methods. Several independent transgenic individuals carrying the SpMas-bn5 and SpMas-bn3 transgenes are assayed for expression by northern analysis. Three independent transgenic individuals from each class are selected as high expressers, and three of each control transformant class are also selected. Crosses are done between 1) SpMas-bn5 transgenic plants and pNG5185 transgenic plants, 2) SpMas-bn3 transgenic plants and pWTT2200 transgenic plants, and 3) SpMas-bn5 and SpMas-bn3 transgenic plants. Only in the third set of crosses would a functional cell lethal function be expressed in those cells which carry both the SpMas-bn5 and SpMas-bn3 genes. This represents one-fourth of the progeny population.

Thus, in cross (1) and (2), kanamycin-resistant, chlorsulfuron resistant and doubly-resistant progeny are expected. However, in cross (3), only kanamycin-resistant and chlorsulfuron resistant progeny are expected, with the doubly-resistant zygotes being killed by reconstitution of barnase activity.

EXAMPLE 4

Example 4 describes tobacco lines expressing an amino-terminal barnase partial peptide and a carboxy-terminal barnase partial peptide under control of a promoter expressed in seed coats.

As described in example 1, chimeric genes are prepared in which bn5 and bn3 coding sequences are each operably linked to a seed coat promoter isolated from watermelon, and known as pWM403. A 2 kbp fragment of the region preceeding the start of transcription of the WM403 gene is used for each chimeric gene. The individual bn5 and bn3 chimeric genes are cloned into plant binary vectors pWTT2200 and pNG5185 respectively, as described in example 3 above. Three independent transgenic individuals from each class are selected as high expressers, and three transgenic individuals of each control transformant class (vector only) are also selected. Crosses are made between 1) pWM403-bn5 transgenic plants and pNG5185 transgenic plants, 2) pWM403-bn3 transgenic plants and pWTT2200 transgenic plants, and 3) pW M403-bn5 and pWM403-bn3 transgenic plants. Progeny plants resistant to both chlorsulfuron and kanamycin are selected and grown to maturity for evaluation of seed and seed coat development.

EXAMPLE 5

Example 5 describes tobacco lines expressing an amino-terminal barnase partial peptide and a carboxy-terminal barnase partial peptide under control of two different promoters expressed in seed coats.

As described in example 1, chimeric genes are prepared in which bn5 and bn3 coding sequences are each operably linked to a seed coat promoter isolated from tobacco, and known as pT218 (Fobert et al., *The Plant Journal* 6:567–77 (1994)). A 2 kbp fragment of the T218 promoter is used for each chimeric gene. As described in example 4, bn5 and bn3 chimeric genes are cloned into the plant binary vectors pWTT2200 and pNG5185 respectively. High expressing transgenic individuals are identified as described in example 4. Crosses are made between 1) pT218-bn5 transgenic plants and pNG5185 transgenic plants, 2) pT218-bn3 transgenic plants and pWTT2200 transgenic plants, 3) pT218-bn5 and pWM403-bn3 transgenic plants, and 4) pWM403-bn5 and pT218-bn3 transgenic plants. Progeny plants resistant to both chlorsulfuron and kanamycin are selected and grown to maturity for evaluation of seed and seed coat development.

EXAMPLE 6

Example 6 describes tobacco lines expressing an amino-terminal barnase partial peptide and a carboxy-terminal barnase partial peptide under control of a promoter expressed in tapetal cells.

As described in example 1, chimeric genes are prepared in which bn5 and bn3 coding sequences are each operably linked to a tapetal-specific promoter isolated from tobacco, and known as pTA29 (Mariani et al., *Nature* 347:737–41, (1990)). As described in example 4, bn5 and bn3 chimeric genes are cloned into the plant binary vectors pWTT2200 and pNG5185, respectively. High expressing transgenic individuals are identified as described in example 4. Crosses are made between 1) pTA29-bn5 transgenic plants and pNG5185 transgenic plants, 2) pTA29-bn3 transgenic plants and pWTT2200 transgenic plants, and 3) pTA29-bn5 and pTA29-bn3 transgenic plants. Progeny plants resistant to both chlorsulfuron and kanamycin are selected and grown to maturity for evaluation of pollen development and male fertility.

EXAMPLE 7

Example 7 describes development of two-component system based on colicin E7 nuclease function.

Gene sequences are known for four colicins that share extensive sequence homology over the latter 210 amino acids of their sequence, with the amino terminal portion of the colicins being very different. A region of approximately 15,000 daltons of the carboxy terminal end of the colicins comprises a non-specific nuclease function known to be involved in the cell death of cells into which the nuclease is targeted via the amino terminal segment. Alignment of these sequences reveals a region of approximately 30 amino acids located 65–35 amino acids from the carboxy terminus which is highly variable. Within this region of colicin is a methionine residue 55 amino acid residues from the carboxy terminus of the protein.

Based on the known sequence of colicin E7, the 5' coding sequence is created, through polymerase chain reaction, by incorporating a methionine codon in place of the leucine codon located at position 135 residues from the carboxy terminus, with a stop codon inserted in place of the methionine codon at residue 55 from the carboxy terminus. The 3' coding sequence is created, through polymerase chain reaction, using the methionine codon at residue 55 from the carboxy terminus as the initiation codon and using the normal stop codon of the colicin E7 message. Other two-component candidates are made in a similar fashion but replacing 1) the threonine at position 48 residues from the carboxy terminus with a stop codon for the 5' coding sequence and with a methionine codon for the 3' coding sequence, or 2) the valine at position 43 residues from the carboxy terminus with a stop codon for the 5' coding sequence and with a methionine codon for the 3' coding sequence. Similar amino acid replacements are made in the same region to produce a range of other candidate two-component systems.

Each pair of coding sequences is cloned, as described in example 1, into a vector with the SpMas promoter to create genes that are constitutively expressed in plant cells. The pair of candidate genes is then introduced biollistically into plant leaf disks either separately or in combination as shown in example 2.

EXAMPLE 8

Example 8 describes a two-component system for the reconstitution of a lethal function in plant cells.

Example 8A

Example 8A describes the subcloning of two partial barnase genes (bn3 and bn5) using the 35S promoter, and the subcloning of a barstar gene using a enhanced 35S promoter.

The partial bn3 and bn5 genes operably linked to the 35S promoter were subcloned in the following manner. Plasmids pER4013 (SpMAS-bn5, encoding the barnase gene bn5) and pER4022 (SpMAS-bn3, encoding the barnase gene bn3) were digested with NcoI and XbaI, and the fragments corresponding to the bn5 and bn3 coding regions were gel purified. Plasmid pEL5051, which contains a 35S-Gus synthetic gene, was digested with NcoI and XbaI, which excised the GUS coding region. The remaining NcoI/XbaI fragment from pEL5051, containing the 35S promoter, was then gel purified. The bn3 and bn5 fragments were then each separately cloned into this NcoI/XbaI fragment of pEL5051 to make pEL5152 and pEL5161, which respectively encode bn3 and bn5, each linked to the 35S promoter.

The barstar gene operably linked to the enhanced 35S promoter was subcloned in the following manner. The complete barstar coding sequence from *Bacillus amyloliquefaciens* is available from GenBank under Accession No. X15545 (Hartley, *J. Mol. Biol.* 202:913–915 (1988)). First, a complete coding sequence of barstar was obtained. To produce a coding sequence that included the complete functional barstar, PCR primers corresponding to the ends of the barstar coding sequence were made. These primers contained additional restriction sites for BspHI at the 5' end and XbaI at the 3' end. The primers were used for PCR amplifications using *Bacillus amyloliquefaciens* genomic DNA with TAQ DNA polymerase according to the manufacturer's recommendations. *Bacillus amyloliquefaciens* strain ATCC No. 23842 chromosomal DNA was isolated according to standard methods. The PCR fragments were digested with BspHI and XbaI and the fragment with the barstar coding sequence was gel purified and cloned into pUC120 digested with NcoI and XbaI.

At least two plasmids were identified by restriction digest as having the correct size insert band. These plasmids were sequenced and one plasmid with the correct barstar sequence was designated pNG5011. Plasmid pNG5011 was used as a source of DNA for a second round of PCR amplification as described above, except that Vent DNA polymerase was used. The resulting fragments were gel purified and cloned into EcoRV-digested pBluescript plasmid. At least two plasmids identified by restriction digest as having the correct size fragment were sequenced and the correct barstar sequence was confirmed for at least one of these clones. This plasmid was designated pBH4004. Plasmid pBH4004 was digested with BspHI and XbaI and the fragment corresponding to barstar was gel purified.

Second, the enhanced 35S promoter was obtained. Plasmid pKL3049 contains a synthetic gene comprised of a 35S promoter with two copies of an 35S enhancer region (this promoter is designated e35S or enhanced 35S) attached at an NcoI restriction site to a chitinase coding sequence, ChiA, which is joined to a NOS 3' region at a XbaI restriction site. Plasmid pKL3049 was digested with NcoI and XbaI and the fragment containing the e35S promoter was gel purified. This gel purified fragments containing the e35S promoter was ligated to the gel purified barstar fragment described above, and the resulting plasmid was designated pSG5351, which constitutes a e35S-barstar synthetic gene.

Example 8B

Example 8B describes a biollistics assay for the reconstitution of a lethal function in plant cells. This example shows that the lethal function is due to the RNase activity of a reconstituted barnase. This reconstitution was demonstrated by the specific reduction of this lethal function with co-expression of barstar, the specific inhibitor of the RNase activity of barnase.

Reconstitution of cell lethality was assayed by bombarding plant leaves with a mixture of pEL5152 and pEL5161 plasmid DNA along with DNA of the plasmid pJJ3792, which comprises a 35S-LUC chimeric gene. To demonstrate that this reconstituted activity is responsive to the inhibition of the RNase activity of barnase, plant leaves were bombarded with a mixture of pEL5152, pEL5161 and pSG5351, along with pJJ3792. As controls, pEL5152, pEL5161, and pSG5351 were delivered biollistically, separately, with pJJ3792.

The plasmid DNAs were prepared as double stranded circular molecules purified by two rounds of CsCl density gradient centrifugation. After determining the DNA concentration by spectrophotometer, the concentration of each plasmid was adjusted to 400 mg/ml in 10 mM tris 1 mM EDTA, pH 8.0. The plasmids were mixed according to standard methods as described in example 2, except that 40 µL of each DNA mixture was mixed with 20 µL of tungsten particles, 20 µL of 100 mM spermidine, and 50 µL of 2.5 M CaCl2. After centrifugation, the particles were suspended in 50 µL of 70% ethanol. The 40 µL DNA mixture contained 4 µL of pJJ3792 and 12 µL of pEL5152, pEL5161, or pSG5351 either separately or together. A CsCl purified filler DNA was used to bring the volume for each sample to 40 µL.

Bombardment was performed as described in example 2, except that tobacco leaf disk are used and the helium pressure was 150 psi. Luciferase assays were performed as described in example 2 except that plant leaf extracts were prepared in 200 µL of Cell Lysis Buffer (Promega), the samples were centrifuged, and then 20 µL of the supernatant was diluted to 100 µL with Cell Lysis Buffer. The assay used 40 µL of assay solution and 5 µL of diluted plant extract. Typical luciferase assay results are shown in Table 5 and are reported as the average cpm for 10 leaf disk per treatment.

The combination of 35S-bn5 and 35S-bn3 resulted in an 86% reduction in luciferase activity as compared with the average of the three controls. The addition of e35S-barstar to 35S-bn3 and 35S-bn5 resulted in a restoration of luciferase activity to 48% of the average of the controls. This result indicates that the cell lethal function reconstituted by the expression of bn5 and bn3 in the same cell is the RNase activity of barnase.

TABLE 5

Luciferase activity recorded as the cpm per tobacco leaf disk and as the average cpm for 10 tobacco leaf disks. Values are (measured cpm minus background) × .001.

| Gene construct | bn3 | bn5 | barstar | bn3 + bn5 | bn3 + bn5 + barstar |
|---|---|---|---|---|---|
| shot 1 | 166 | 288 | 442 | 6 | 89 |
| shot 2 | 125 | 336 | 79 | 88 | 133 |
| shot 3 | 649 | 1,252 | 534 | 84 | 143 |
| shot 4 | 793 | 2,577 | 1,352 | 136 | 100 |
| shot 5 | 321 | 1,714 | 1,229 | 208 | 165 |
| shot 6 | 124 | 1,170 | 1,562 | 174 | 959 |
| shot 7 | 1,394 | 738 | 2,068 | 138 | 1,265 |
| shot 8 | 1,101 | 1,562 | 1,432 | 297 | 1,355 |
| shot 9 | 1,244 | 1,428 | 1,307 | 247 | 977 |
| shot 10 | 649 | 5,627 | 512 | 155 | 219 |
| average | 657 | 1,669 | 1,052 | 153 | 540 |

EXAMPLE 9

Example 9 describes improvement in function of the two-component system through site-specific mutagenesis.

Example 9A

Example 9A describes construction of chimeric genes that encode mutagenized peptides for enhanced stability.

For the bn5 gene, specific nucleotide changes were introduced so that the amino acid sequence was changed from MAQVINTFDGVADYL QTYHKLPDNYITKSEAQALGW (SEQ ID NO:1) to MAQVINTFDGVADYLIRYHKLPDNYITKSEAQALGW (SEQ ID NO:2). The glutamine residue at position 16 of bn5 (position 15 of mature barnase protein) was replaced by an isoleucine residue, and the arginine residue at position 17 of bn5 (position 16 of mature barnase protein) was replaced by an arginine residue (changes underlined). For the bn3 sequence, specific nucleotide changes were introduced so that the amino acid sequence was changed from MASKGN-LADVAPGKSIGGDIFSNRE GKLPGKSGRTWREADINYTSGFRNSDRILYSSDWLI YKTTDHYQTFTKIR (SEQ ID NO:3) to MASKGNLAD-VAPGKSIGGDIFSNRE SKLPGKSGRTWREADINYTSGFRNSDRILYSSDWLI YKTTDHYQTFTRIR (SEQ ID NO:4). The glycine residue at position 30 of bn3 (position 65 of mature barnase protein) was replaced by a serine residue, and the lysine residue at position 73 of bn3 (position 108 of mature base protein) was replaced by an arginine residue (changes underlined).

The nucleotide changes were introduced by PCR, using the same general methods of example 1. To create the modified bn5 sequence, two PCR reactions were performed, using a barnase coding sequence-containing plasmid as template, one with primers NC207 and NC225, the other with NC224 and NC143. NC207:5' GGCCATGGCACAG-GTTATCAACACGTTTGACGGGGTTGC 3' (SEQ ID NO:5) NC225: 5' AGGAAGCTTATGATATCTGATAA-GATAATCCGCAACCCCG 3' (SEQ ID NO:6) NC224: 5' CATAAGCTTCCTGATAATTACATTACAAAATC 3' (SEQ ID NO:7) NC143: 5' CGTCTAGATTACCAGC-CGAGGGCTTGTGCTTC 3' (SEQ ID NO:8).

The resulting DNA fragments were gel purified and then mixed together prior to performing a PCR reaction with primer pair NC207 and NC143. The resulting fragment was digested with HindIII to confirm the fragment identity and then digested with NcoI and XbaI prior to cloning into pUC120. The resulting plasmid, comprising the full, modified coding sequence of bn5 (bn5-2), was designated pAR4554. The cloned fragment was sequenced.

To create a modified bn3 sequence, two PCR reactions were performed, using a barnase coding sequence-containing plasmid as template, one with primers NC144 and NC221, and one with NC222 and NC223. NC144: 5' GGCCATGGCATCAAAAGGGAACCTTGCAGA 3' (SEQ ID NO:9) NC221: 5' CCATGTGCGGC-CGCTTTTGCTCGGGAGTTGCCTTC 3' (SEQ ID NO:10) NC222: 5' AAAAGCGGCCGCACATGGCGTGAAGCG-GATATTAACTATGTATCAGGCTTCAG 3' (SEQ ID NO:11) NC223: 5' CGTCTAGAGTTATCTGATCCTTG-TAAAGGTCTG 3' (SEQ ID NO:12).

The resulting DNA fragments were gel purified and then mixed together prior to performing a PCR reaction with primer pair NC144 and NC223. The resulting fragment was digested with NotI to confirm the fragment identity and then digested with NcoI and XbaI prior to cloning into pUC120. The resulting plasmid, comprising the full, modified coding sequence of bn3 (bn3-2), was designated pAR4561. The cloned fragment was sequenced.

In order to create chimeric genes that express the modified bn5 and modified bn3 peptides constitutively in plants, plasmids pAR4554 and pAR4561 were digested with NcoI and XbaI, the suitable fragments were gel purified, and each was inserted into plasmid pEL5051, with the bn5-2 and bn3-2 coding sequences replacing the coding sequence of the beta-glucuronidase (uidA) gene removed by NcoI-XbaI digestion and gel purification of the resulting large fragment. The resulting chimeric genes have each partial coding sequence operably linked to the CaMV 35S promoter and to the 3' polyadenylation region of the octopine synthase gene. The size of the inserted fragments was verified by agarose gel electrophoresis. The plasmid containing the chimeric bn5-2 gene was designated pEL5061, and the plasmid containing the chimeric bn3-2 gene was designated pEL5071.

Example 9B

Example 9B describes biollistics assays to determine activity of the two modified peptides compared with the unmodified peptides in plant cells.

Reconstitution of ribonuclease activity is assayed as described in example 8, by the biollistics delivery of the two partial genes together in comparison with the 2 partial genes individually. This is done in a single experiment, with leaf tissue of a young tobacco plant as the target for DNA delivery. The data from a typical experiment are shown in Table 6. When the modified barnase fragments were expressed in the same cell, the luciferase activity was reduced to 19% of the average of the four controls. When the unmodified barnase fragments were expressed in the same cell, the luciferase activity was reduced to less than 56% of the average of the four controls.

TABLE 6

Luciferase activity recorded as cpm per tobacco leaf disk and as the average for 11 leaf disks per treatment. Data is reported as (measured cpm minus background) × .001.

| Gene construct | bn5-2 | bn3-2 | bn5 | bn3 | bn5-2 + bn3-2 | bn5 + bn3 |
|---|---|---|---|---|---|---|
| shot 1 | 120 | 123 | 79 | 214 | 32 | 76 |
| shot 2 | 289 | 115 | 124 | 68 | 53 | 75 |
| shot 3 | 78 | 107 | 217 | 115 | 44 | 111 |
| shot 4 | 221 | 341 | 308 | 261 | 139 | 134 |
| shot 5 | 583 | 162 | 156 | 543 | 52 | 218 |
| shot 6 | 232 | 401 | 958 | 461 | 32 | 143 |
| shot 7 | 1,265 | 970 | 1,079 | 311 | 59 | 191 |
| shot 8 | 769 | 844 | 1,202 | 342 | 76 | 272 |
| shot 9 | 127 | 145 | 832 | 402 | 100 | 140 |
| shot 10 | 205 | 161 | 742 | 1,912 | 60 | 334 |
| shot 11 | 144 | 232 | 291 | 974 | 65 | 422 |
| average | 367 | 327 | 544 | 509 | 65 | 193 |

Reconstitution of ribonuclease activity was also assayed with leaf tissue of a young pepper plant as the target for DNA delivery. The data from one experiment are shown in Table 7. When the modified barnase fragments were expressed in the same cell, the luciferase activity was reduced to 9% of the average of the four controls. When the unmodified barnase fragments were expressed in the same cell, the luciferase activity was reduced to 60% of the average of the four controls.

TABLE 7

Luciferase activity recorded as cpm minus background per pepper leaf disk and as the average for 8 leaf disks per treatment. Data is reported as (measured cpm minus background) × .001.

| Gene construct | bn5-2 | bn3-2 | bn5 | bn3 | bn5-2 + bn3-2 | bn5 + bn3 |
|---|---|---|---|---|---|---|
| shot 1 | 3 | 6 | 23 | 41 | 8 | 20 |
| shot 2 | −2 | 24 | 275 | 16 | 5 | 16 |
| shot 3 | 34 | 87 | 44 | 20 | 11 | 69 |
| shot 4 | 440 | 95 | 217 | 156 | 10 | 69 |
| shot 5 | 61 | 130 | 146 | 32 | 4 | 6 |
| shot 6 | 16 | 83 | 42 | 26 | 18 | 59 |
| shot 7 | 47 | 122 | 29 | 7 | 5 | 199 |
| shot 8 | 325 | 77 | 348 | 8 | 6 | 10 |
| average | 115 | 78 | 140 | 38 | 8 | 56 |

Example 9C

Example 9C describes biollistics assays to determine the relative activity of the 2 modified peptides compared with the unmodified peptides in plant cells.

A dilution experiment was performed, with decreasing amounts of the 2 modified partial genes used for DNA delivery. This was done in a single experiment, with leaf tissue of a young pepper plant as the target for DNA delivery as described in example 8. The data from a typical experiment are shown in Table 8. The modified barnase fragments bn5-2 and 3-2, when used together at 2, 6 and 18 µL, have 60%, 17% and 9% of the luciferase activity of the average value of the four controls. The unmodified barnase fragments bn5 and bn3, when used together at 18 µL have 60% of the luciferase activity of the average value of the four controls. Approximately 10% of the amount of the modified partial genes gives equal reduction in LUC activity compared with the standard amounts of the 2 unmodified partial genes. Similar data were obtained when this experiment was repeated.

TABLE 8

Luciferase activity recorded as cpm per pepper leaf disk and as the average for 8 leaf disks per treatment. Data is reported as (measured cpm minus background) × .001.

| Gene construct | bn5-2 | bn3-2 | bn5 | bn3 | 2 μL bn5-2 +bn3-2 | 6 μL bn5-2 +bn3-2 | 18 μL bn5-2 +bn3-2 | 18 μL bn5-2 +bn3-2 |
|---|---|---|---|---|---|---|---|---|
| shot 1 | 3 | 6 | 23 | 41 | 88 | 5 | 8 | 20 |
| shot 2 | −2 | 24 | 275 | 16 | 19 | 10 | 5 | 16 |
| shot 3 | 34 | 87 | 44 | 20 | 46 | 18 | 11 | 69 |
| shot 4 | 440 | 95 | 217 | 156 | 12 | 45 | 10 | 69 |
| shot 4 | 61 | 130 | 146 | 32 | 56 | 29 | 4 | 6 |
| shot 6 | 16 | 83 | 42 | 26 | 194 | 17 | 18 | 59 |
| shot 7 | 47 | 122 | 29 | 7 | 21 | 5 | 5 | 199 |
| shot 8 | 325 | 77 | 348 | 8 | 1 | 2 | 6 | 10 |
| average | 115 | 78 | 140 | 38 | 55 | 16 | 8 | 56 |

Experiment 9D

Experiment 9D describes biollistics assays to determine activity of the 2 modified peptides compared with the unmodified peptides in pea pod tissue.

Reconstitution of ribonuclease activity in pea pod tissue was assayed as described in example 8, by the biollistics delivery of the 2 partial genes together in comparison with a luciferase with filler DNA only control. This was done in a single experiment, with tissue from the inner surface of immature pea pods as the target for DNA delivery. The data from a typical experiment are shown in Table 9. When the modified barnase fragments are expressed in the same cell, the luciferase activity is reduced to 2% of the Luc controls.

TABLE 9

Luciferase activity recorded as cpm per pea pod disk and as the average for 12 disks per treatment. Data is reported as (measured cpm minus background) × .001.

| Gene construct | LUC with filler DNA | LUC with bn5-2 and bn3-2 |
|---|---|---|
| shot 1 | 3,987 | 643 |
| shot 2 | 38,575 | 57 |
| shot 3 | 16,964 | 162 |
| shot 4 | 13,852 | 51 |
| shot 5 | 19,809 | 98 |
| shot 6 | 7,964 | 8 |
| shot 7 | 15,988 | 81 |
| shot 8 | 15,495 | 2,060 |
| shot 9 | 9,635 | 79 |
| shot 10 | 20,903 | 124 |
| shot 11 | 32,932 | 512 |
| shot 12 | 17,476 | 748 |
| average | 17,798 | 385 |

Example 9E

Example 9E describes biollistics assays to determine activity of the two modified peptides compared with the unmodified peptides in pea seed coat tissue.

Reconstitution of ribonuclease activity in pea seed coat tissue was assayed as described in example 8, by the biollistics delivery of the two partial genes together in comparison with a luciferase with filler DNA only control. This was done in a single experiment, with tissue from imnature pea seeds (less than 0.9 cm in diameter) as the target for DNA delivery. The data from one experiment are shown in Table 10. When the modified barnase fragments were expressed in the same cell, the luciferase activity was reduced to 2% of the Luc controls.

TABLE 10

Luciferase activity recorded as cpm per pea seed coat and as the average for 6 disks per treatment. Data is reported as (measured cpm minus background) × .001.

| Gene construct | LUC with filler DNA | LUC with bn5-2 and bn3-2 |
|---|---|---|
| shot 1 | 29,675 | 176 |
| shot 2 | 35,205 | 543 |
| shot 3 | 8,190 | 4 |
| shot 4 | 4,646 | 278 |
| shot 5 | 1,477 | 135 |
| shot 6 | 980 | 227 |
| average | 13,362 | 227 |

EXAMPLE 10

Example 10 describes that when the two partial genes are introduced into tobacco cells by Agrobacterium, cell lethality results.

Plasmids carrying the bn5 and bn3 chimeric genes, e.g., as described in example 9A, are digested to liberate the chimeric genes themselves. The chimeric genes are each inserted at an appropriate restriction site in a T-DNA vector.

In addition, a control lethality gene is used which has a barnase coding sequence disrupted by an intron to prevent bacterial expression of barnase activity. For instance, the st-1s ivs2 intron used by Vancanneyt et al., *Mol. Gen. Genet.* 220:245–50 (1990) is inserted into the valine codon at position 36 of the mature barnase protein (position 37 of the barnase gene used here, due to the addition of a methionine residue prior to the alanine residue of the mature barnase protein). A chimeric gene is constructed using the barnase coding sequence with the intron operably linked to the CaMV 35S promoter and to the octopine synthase 3' untranslated region at the 3' end. An appropriate T-DNA vector is prepared from this construct.

Young tobacco leaf plants are used for Agrobacterium-mediated DNA delivery, according to standard techniques, of 1) 35S-bn5 by itself, 2) 35S-bn3 by itself, 3) 35S-bn5/35S-bn3 together, or 4) 35S-barnaseINT. An Agrobacterium colony containing the appropriate plasmid, each from a fresh plate is used to inoculate 5 ml of LB containing 10 μg per ml tetracycline. These cultures are grown at 28° C. for 48 hours. One ml of each culture is then transferred into separate flasks with 50 ml of LB containing 20 μM acetosyringone and 10 μg per ml of tetracycline. These cultures are grown at 28° C. for 16 hours. The cells are then spun down in a table top centrifuge for 30 min. and the cells are suspended in 50 ml of MS salts with 3% sucrose, 0.5 mM MES pH 5.6 and 10 μM acetosyringone. The OD at 600 nm is adjusted to 1 to 1.5. Cells are then left at room temperature for up to 3 hours before injection into leaves.

Tobacco leaves 7 to 10 cm in length are nicked only on the underside and Agrobacterium bacteria is infiltrated into the leaf by filling a 1 ml syringe with Agrobacterium and placing the syringe tip (with no needle) tight against the nick. Pressure is applied to the syringe plunger and the sector in the leaf between the mid-rib and two lateral veins is infused with the Agrobacterium solution. The introduction of the Agrobacterium solution is monitored by the change in color of the leaf from green to dark green when the solution is introduced.

After approximately 5 days of incubation at room temperature, cell death can be observed by chlorosis and browning followed by complete tissue collapse. Neither the bn5 nor bn3 chimeric genes individually give rise to cell death. However, when the bn5 and bn3 chimeric genes are introduced together or when intact barnaseINT is introduced, cell death is observed. Precise timing of cell death can vary.

All publications and patents mentioned in this specification are herein incorporated by reference into the specification to the same extent as if each individual publication or patent was specifically and individually indicated to be incorporated herein by reference.

What is claimed is:

1. A plant containing a plant cell comprising a first expression cassette comprising a first plant promoter operably linked to a first polynucleotide encoding a first polypeptide and a second expression cassette comprising a second plant promoter operably linked to a second polynucleotide encoding a second polypeptide, wherein at least the first or the second plant promoter is a non-constitutive promoter, wherein the first and second polypeptides each comprise a separate but complementary amino acid subsequence of a single functional nuclease polypeptide and wherein expression of both the first and second polypeptides in the same cell results in production of a functional nuclease, thereby impairing cellular function.

2. The plant of claim 1, wherein the first or the second promoter is a tissue-specific promoter.

3. The plant of claim 1, wherein the first and second promoters are each functional in seeds.

4. The plant of claim 1, wherein the first and second promoters are each functional in tapetal cells.

5. The plant of claim 1, wherein the first or second promoter is induced following interaction with a plant pathogen or pest.

6. The plant of claim 1, wherein the functional polypeptide is a ribonuclease.

7. The plant of claim 6, wherein the ribonuclease is Barnase.

8. The plant of claim 7, wherein the Barnase has enhanced stability.

9. The plant of claim 7, wherein the Barnase is bn3-2 and bn5-2.

10. The plant of claim 6, wherein the ribonuclease is ribonuclease T1.

11. The plant of claim 1, wherein the functional nuclease polypeptide is colicin.

12. The plant of claim 1, wherein the first and second promoters have different but overlapping specificities.

13. A method of impairing cellular function in a plant cell, the method comprising the step of:

introducing into a plant cell a first expression cassette comprising a first plant promoter operably linked to a first polynucleotide encoding a first non-functional polypeptide and a second expression cassette comprising a second plant promoter operably linked to a second polynucleotide encoding a second non-functional polypeptide, wherein at least the first or the second plant promoter is a non-constitutive promoter, wherein the first and second polypeptides each comprise a separate but complementary amino acid subsequence of a single functional nuclease polypeptide and wherein expression of both the first and second polypeptides in the same cell results in expression of a functional nuclease, thereby impairing cellular function.

14. The method of claim 13, wherein the first and second promoters are each functional in seeds.

15. The method of claim 13, wherein the first and second promoters are each functional in tapetal cells.

16. The method of claim 13, wherein the first or the second expression cassettes is introduced into the plant cell through a sexual cross.

17. The method of claim 13, wherein the functional polypeptide is a ribonuclease.

18. The method of claim 17, wherein the ribonuclease is Barnase.

19. The method of claim 18, wherein the Barnase has enhanced stability.

20. The method of claim 18, wherein the Barnase is bn3-2 and bn5-2.

21. The method of claim 17, wherein the ribonuclease is ribonuclease T1.

22. The method of claim 13, wherein the functional nuclease polypeptide is colicin.

23. The method of claim 13, wherein the first and second promoters have different but overlapping specificities.

24. The plant of claim 1, wherein both the first and the second plant promoters are non-constitutive.

25. The method of claim 13, wherein both the first and the second plant promoters are non-constitutive.

* * * * *

```
                         SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp
        35

(2) INFORMATION FOR SEQ ID NO: 2:

(i) SEQUENCE CHARACTERISTICS:
        (A) LENGTH: 36 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Met Ala Gln Val Ile Asn Thr Phe Asp Gly Val Ala Asp Tyr Leu Ile
1               5                   10                  15

Arg Tyr His Lys Leu Pro Asp Asn Tyr Ile Thr Lys Ser Glu Ala Gln
            20                  25                  30

Ala Leu Gly Trp
        35

(2) INFORMATION FOR SEQ ID NO: 3:

(i) SEQUENCE CHARACTERISTICS:
        (A) LENGTH: 75 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Met Ala Ser Lys Gly Asn Leu Ala Asp Val Ala Pro Gly Lys Ser Ile
1               5                   10                  15
```

```
Gly Gly Asp Ile Phe Ser Asn Arg Glu Gly Lys Leu Pro Gly Lys Ser
            20                  25                  30

Gly Arg Thr Trp Arg Glu Ala Asp Ile Asn Tyr Thr Ser Gly Phe Arg
        35                  40                  45

Asn Ser Asp Arg Ile Leu Tyr Ser Ser Asp Trp Leu Ile Tyr Lys Thr
    50                  55                  60

Thr Asp His Tyr Gln Thr Phe Thr Lys Ile Arg
65                  70                  75

(2) INFORMATION FOR SEQ ID NO: 4:

(i) SEQUENCE CHARACTERISTICS:
        (A) LENGTH: 75 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Met Ala Ser Lys Gly Asn Leu Ala Asp Val Ala Pro Gly Lys Ser Ile
1               5                   10                  15

Gly Gly Asp Ile Phe Ser Asn Arg Glu Ser Lys Leu Pro Gly Lys Ser
            20                  25                  30

Gly Arg Thr Trp Arg Glu Ala Asp Ile Asn Tyr Thr Ser Gly Phe Arg
        35                  40                  45

Asn Ser Asp Arg Ile Leu Tyr Ser Ser Asp Trp Leu Ile Tyr Lys Thr
    50                  55                  60

Thr Asp His Tyr Gln Thr Phe Thr Arg Ile Arg
65                  70                  75

(2) INFORMATION FOR SEQ ID NO: 5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GGCCATGGCA CAGGTTATCA ACACGTTTGA CGGGGTTGC                               39

(2) INFORMATION FOR SEQ ID NO: 6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

AGGAAGCTTA TGATATCTGA TAAGATAATC CGCAACCCCG                              40

(2) INFORMATION FOR SEQ ID NO: 7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 7:

CATAAGCTTC CTGATAATTA CATTACAAAA TC                                32

(2) INFORMATION FOR SEQ ID NO: 8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CGTCTAGATT ACCAGCCGAG GGCTTGTGCT TC                                32

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GGCCATGGCA TCAAAAGGGA ACCTTGCAGA                                   30

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

CCATGTGCGG CCGCTTTTGC TCGGGAGTTT GCCTTC                            36

(2) INFORMATION FOR SEQ ID NO: 11:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

AAAAGCGGCC GCACATGGCG TGAAGCGGAT ATTAACTATG TATCAGGCTT CAG          53

(2) INFORMATION FOR SEQ ID NO: 12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA -continued (xi) SEQUENCE DESCRIPTION: SEQ ID NO: 12:

CGTCTAGAGT TATCTGATCC TTGTAAAGGT CTG    33